(12) United States Patent
Wagner

(10) Patent No.: US 9,816,100 B2
(45) Date of Patent: Nov. 14, 2017

(54) SOYBEAN SEED AND OIL COMPOSITIONS AND METHODS OF MAKING SAME

(71) Applicant: Monsanto Technology LLC, St. Louis, MO (US)

(72) Inventor: Nicholas William Wagner, Sacramento, CA (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

(21) Appl. No.: 15/267,649

(22) Filed: Sep. 16, 2016

(65) Prior Publication Data

US 2017/0002372 A1     Jan. 5, 2017

Related U.S. Application Data

(62) Division of application No. 12/882,579, filed on Sep. 15, 2010, now Pat. No. 9,480,271.

(60) Provisional application No. 61/242,745, filed on Sep. 15, 2009.

(51) Int. Cl.
| | |
|---|---|
| *C12N 15/82* | (2006.01) |
| *A23D 9/00* | (2006.01) |
| *C12N 9/02* | (2006.01) |
| *A01H 5/10* | (2006.01) |
| *C12N 9/16* | (2006.01) |

(52) U.S. Cl.
CPC .......... *C12N 15/8247* (2013.01); *A01H 5/10* (2013.01); *A23D 9/00* (2013.01); *C12N 9/0083* (2013.01); *C12N 9/16* (2013.01); *C12N 15/8218* (2013.01); *C12Y 114/19* (2013.01); *C12Y 301/02014* (2013.01)

(58) Field of Classification Search
None
See application file for complete search history.

(56) References Cited

U.S. PATENT DOCUMENTS

| | | |
|---|---|---|
| 4,089,880 A | 5/1978 | Sullivan |
| 4,915,972 A | 4/1990 | Gupta et al. |
| 4,948,811 A | 8/1990 | Spinner et al. |
| 5,130,449 A | 7/1992 | Lagarde et al. |
| 5,208,058 A | 5/1993 | Kotani et al. |
| 5,260,077 A | 11/1993 | Carrick et al. |
| 5,278,325 A | 1/1994 | Strop et al. |
| 5,286,886 A | 2/1994 | Van de Sande et al. |
| 5,315,020 A | 5/1994 | Cheng et al. |
| 5,387,758 A | 2/1995 | Wong et al. |
| 5,401,866 A | 3/1995 | Cheng et al. |
| 5,434,283 A | 7/1995 | Wong et al. |
| 5,516,924 A | 5/1996 | van de Sande et al. |
| 5,520,708 A | 5/1996 | Johnson et al. |
| 5,530,183 A | 6/1996 | Fehr et al. |
| 5,534,425 A | 7/1996 | Fehr et al. |
| 5,545,821 A | 8/1996 | Wong et al. |
| 5,625,130 A | 4/1997 | Grant et al. |
| 5,658,767 A | 8/1997 | Kyle |
| 5,696,278 A | 12/1997 | Segers |
| 5,710,365 A | 1/1998 | Kerr et al. |
| 5,710,369 A | 1/1998 | Fehr et al. |
| 5,714,668 A | 2/1998 | Fehr et al. |
| 5,714,669 A | 2/1998 | Fehr et al. |
| 5,714,670 A | 2/1998 | Fehr et al. |
| 5,723,761 A | 3/1998 | Voelker et al. |
| 5,750,844 A | 5/1998 | Fehr et al. |
| 5,763,745 A | 6/1998 | Fehr et al. |
| 5,767,338 A | 6/1998 | Fan |
| 5,795,969 A | 8/1998 | Fehr et al. |
| 5,840,946 A | 11/1998 | Wong et al. |
| 5,850,026 A | 12/1998 | DeBonte et al. |
| 5,850,030 A | 12/1998 | Fehr et al. |
| 5,859,350 A | 1/1999 | DeBonte et al. |
| 5,863,589 A | 1/1999 | Covington, Jr. et al. |
| 5,866,762 A | 2/1999 | DeBonte et al. |
| 5,955,329 A | 9/1999 | Yuan et al. |
| 5,955,650 A | 9/1999 | Hitz |
| 5,965,755 A | 10/1999 | Sernyk et al. |
| 5,969,169 A | 10/1999 | Fan |
| 5,981,781 A | 11/1999 | Knowlton |
| 5,986,118 A | 11/1999 | Fehr et al. |
| 6,022,577 A | 2/2000 | Chrysam et al. |
| 6,063,424 A | 5/2000 | Wells et al. |
| 6,133,509 A | 10/2000 | Fehr et al. |
| 6,147,237 A | 11/2000 | Zwanenburg et al. |
| 6,169,190 B1 | 1/2001 | Lanuza et al. |
| 6,172,248 B1 | 1/2001 | Copeland et al. |
| 6,184,442 B1 | 2/2001 | Nickell |

(Continued)

FOREIGN PATENT DOCUMENTS

| | | |
|---|---|---|
| CA | 2479587 A1 | 10/2003 |
| DE | 2922146 A1 | 7/1980 |

(Continued)

OTHER PUBLICATIONS

Wolf et al 1982 (JAOCS 59:5 p. 230-232).*
Rennie et al 1989 (JAOCS 66:11 p. 1622-1624).*
Heppard et al 1996 (Plant Physiology 110: p. 311-319).*
Kumar et al 2006 (Journal of Food Composition and Analysis 19: p. 188-195).*
Mickel et al., Effect of inert gases on the autoxidation of cis and trans polyunsaturated fatty acid methyl ester Rivista Italiana Della Sostanze Grasse, 53:312-314 (1976).

(Continued)

*Primary Examiner* — Matthew Keogh

(74) *Attorney, Agent, or Firm* — Thompson Coburn LLP; Charles P. Romano; Chunping Li

(57) ABSTRACT

Soybean oil compositions with unique fatty acid profiles are disclosed. These oils can be derived by the suppression of endogenous soybean FAD2 and FAD3 genes and the expression of a stearoyl acyl ACP thioesterase. Soybean plants and seeds comprising these oils are also disclosed.

20 Claims, 5 Drawing Sheets

(56) References Cited

U.S. PATENT DOCUMENTS

| | | |
|---|---|---|
| 6,201,145 B1 | 3/2001 | Fan |
| 6,229,033 B1 | 5/2001 | Knowlton |
| 6,303,849 B1 | 10/2001 | Potts et al. |
| 6,313,328 B1 | 11/2001 | Ulrich et al. |
| 6,331,664 B1 | 12/2001 | Rubin-Wilson et al. |
| 6,340,485 B1 | 1/2002 | Coupland et al. |
| 6,365,802 B2 | 4/2002 | Kridl |
| 6,369,302 B1 | 4/2002 | Matson |
| 6,372,965 B1 | 4/2002 | Lightner et al. |
| 6,376,754 B1 | 4/2002 | Schillinger et al. |
| 6,380,462 B1 | 4/2002 | Kridl |
| 6,384,301 B1 | 5/2002 | Martinell et al. |
| 6,388,110 B1 | 5/2002 | Ulrich et al. |
| 6,388,113 B1 | 5/2002 | Martinez Force et al. |
| 6,426,448 B1 | 7/2002 | Booth, Jr. et al. |
| 6,559,325 B2 | 5/2003 | Fan |
| 6,562,397 B2 | 5/2003 | DeBonte et al. |
| 6,583,303 B1 | 6/2003 | DeBonte et al. |
| 6,593,514 B1 | 7/2003 | Cahoon et al. |
| 6,610,867 B2 | 8/2003 | Jakel et al. |
| 6,667,064 B2 | 12/2003 | Surette |
| 6,713,117 B1 | 3/2004 | Kodali |
| 6,791,016 B1 | 9/2004 | Steiger et al. |
| 6,797,172 B2 | 9/2004 | Koseoglu et al. |
| 6,844,021 B2 | 1/2005 | Koike et al. |
| 6,906,211 B2 | 6/2005 | Tysinger et al. |
| 6,924,381 B2 | 8/2005 | Dawson |
| 7,067,722 B2 | 6/2006 | Fillatti |
| 7,166,771 B2 | 1/2007 | Eenennaam et al. |
| 7,442,850 B2 | 10/2008 | Wu et al. |
| 7,579,492 B2 | 8/2009 | Tysinger |
| 7,741,500 B2 | 6/2010 | Arhancet et al. |
| 7,790,953 B2 | 9/2010 | Fillatti et al. |
| 7,902,388 B2 | 3/2011 | Heise et al. |
| 7,943,818 B2 | 5/2011 | Fillatti et al. |
| 7,973,212 B2 | 7/2011 | Sebastian |
| 8,013,217 B2 | 9/2011 | Wu et al. |
| 8,057,835 B2 | 11/2011 | Makadia et al. |
| 8,378,170 B2 | 2/2013 | Wu et al. |
| 9,480,271 B2 * | 11/2016 | Wagner .............. C12N 9/0083 |
| 2002/0058340 A1 | 5/2002 | Clemente et al. |
| 2003/0024011 A1* | 1/2003 | Dehesh .............. C12N 9/0083 800/281 |
| 2003/0172399 A1 | 9/2003 | Fillatti |
| 2003/0180434 A1 | 9/2003 | Fan |
| 2004/0006792 A1 | 1/2004 | Fillatti et al. |
| 2004/0047971 A1 | 3/2004 | Alander |
| 2004/0049813 A1 | 3/2004 | Russell et al. |
| 2004/0107460 A1 | 6/2004 | Fillatti et al. |
| 2006/0080750 A1 | 4/2006 | Fillatti et al. |
| 2006/0107348 A1 | 5/2006 | Wu et al. |
| 2006/0110521 A1 | 5/2006 | Heise et al. |
| 2006/0111578 A1 | 5/2006 | Arhancet et al. |
| 2006/0206963 A1 | 9/2006 | Voelker et al. |
| 2007/0212780 A1 | 9/2007 | Fillatti |
| 2008/0092251 A1 | 4/2008 | Lightner et al. |
| 2008/0222756 A1 | 9/2008 | Fillatti et al. |
| 2009/0193547 A1 | 7/2009 | Wu et al. |
| 2009/0214744 A1 | 8/2009 | Kridl |
| 2011/0067149 A1 | 3/2011 | Wagner |
| 2011/0239335 A1 | 9/2011 | Fillatti et al. |
| 2012/0028255 A1 | 2/2012 | Wu et al. |
| 2012/0058235 A1 | 3/2012 | Makadia et al. |
| 2013/0067621 A1 | 3/2013 | Fillatti et al. |

FOREIGN PATENT DOCUMENTS

| | | |
|---|---|---|
| EP | 0077528 A1 | 4/1983 |
| EP | 0226245 A1 | 6/1987 |
| EP | 0323753 A1 | 7/1989 |
| EP | 0326198 A2 | 8/1989 |
| EP | 0347056 A1 | 12/1989 |
| EP | 0348004 A2 | 12/1989 |
| EP | 0476093 A1 | 3/1992 |
| EP | 0526954 A2 | 2/1993 |
| EP | 0606359 A1 | 7/1994 |
| EP | 0639333 A1 | 2/1995 |
| EP | 0672096 A1 | 9/1995 |
| EP | 0813357 A1 | 12/1997 |
| EP | 0833882 A1 | 4/1998 |
| EP | 0936266 A1 | 8/1999 |
| EP | 1161877 A1 | 12/2001 |
| EP | 1794309 A1 | 6/2007 |
| GB | 715352 A | 9/1954 |
| GB | 2241503 A | 9/1991 |
| JP | S63-44843 | 2/1988 |
| JP | 10-191885 A | 7/1998 |
| WO | 93/19626 A1 | 10/1993 |
| WO | 9411516 A1 | 5/1994 |
| WO | 96/36684 A1 | 11/1996 |
| WO | 9740698 A1 | 11/1997 |
| WO | 99/58689 A1 | 11/1999 |
| WO | 99/64614 A2 | 12/1999 |
| WO | 00/44862 A1 | 8/2000 |
| WO | 01/14538 A2 | 3/2001 |
| WO | 02/092073 A1 | 11/2002 |
| WO | 03/049832 A1 | 6/2003 |
| WO | 03/080802 A2 | 10/2003 |
| WO | 2004/000871 A2 | 12/2003 |
| WO | 2004/001000 A2 | 12/2003 |
| WO | 2004/001001 A2 | 12/2003 |
| WO | 2004/009827 A2 | 1/2004 |
| WO | 2004/071467 A2 | 8/2004 |
| WO | 2006039449 A1 | 4/2006 |
| WO | 2007/106728 A2 | 9/2007 |

OTHER PUBLICATIONS

Sayanova et al., Identification of primula fatty acid desaturases with n-3" FEBS Letters, 542:100-104, 2003.
Invitation/Partial Search Report issued in analogous application No. PCT/US2005/039809 dated Apr. 7, 2006.
Wilson et al., "Effect of Controlled Atmosphere Storage on Aflatoxin Production in High Moisture Peanuts (Groundnuts)," J. Stored Prod. Res., 12:97-100, 1976.
PCT International Search Report for analogous application No. PCT/US2005/039809 dated Jun. 13, 2006.
List et al., "Potential Margarine Oils from Genetically Modified Soybeans," JAOCS, 73(6):729-732, 1996.
Mounts et al., "Performance Evaluation of Hexane-Extracted Oils from Genetically Modified Soybeans," JAOCS, 71 (2):157-161, 1994.
Yan et al., "Extraction and Refining of Black Currant Seed Oil," China Oils and Fats, 29(2):1-5, 2004.
List et al., "Oxidation and Quality of Soybean Oil: A Preliminary Study of the Anisidine Test," JAOCS, 51:17-21, 1974.
Chu et al., "Factors Affecting the Content of Tocopherol in Soybean Oil," JAOCS, 70(12):1263-1268, 1993.
Neff et al., "Oxidative Stability of Natural and Randomized High-Palmitic- and High-Stearic-Acid Oils from Genetically Modified Soybean Varieties," JAOCS, 76(7):825-831, 1999.
Bhatia et al., "Oilseed cutivars developed from induced mutations and mutations altering fatty acid composition", Mutation Breeding Review, Dec. 1999, pp. 1-36, No. 11, Retrieved from Internet— http://mvgs.iaea.org/pdf/MBREV19991211.pdf.
Warner et al., "Effect of Fatty Acid Composition of Oils on Flavor and Stability of Fried Foods", JAOCS, 1997, p. 347-356, vol. 74(4).
Non-Final Office Action in Inter Partes Reexamination; dated Aug. 14, 2012; Control No. 95/002028.
Comments by Third-Party Requester to Response to Non-Final Office Action in Inter Partes Reexamination; dated Nov. 14, 2012; Control No. 95/002028.
Non-Final Office Action in Inter Partes Reexamination; dated Dec. 7, 2012; Control No. 95/000690.
2nd Declaration of Anthony John Kinney dated Sep. 11, 2012.
Invitation/Partial Search Report issued in analogous application No. PCT/US2005/039807 dated Apr. 7, 2006.
Rafalski, "Applications of Single Nucleotide Polymorphisms in Crop Genetics", Curr. Opin. in Plant Biol., (5): 94-100, 2002.

(56) References Cited

OTHER PUBLICATIONS

Rahman et al.,"Inheritance of Reduced Linolenic Acid Content in Soybean Seed Oil", Theor. Appl. Genet., (94), 299-302, 1997.
Stojsin et al.,"Inheritance of Low Linolenic Acid Level in the Soybean Line RG10", Crop Sci., (38), 1441-1444, 1998.
Petition to Strike Under 37 CFR 1.182; dated Mar. 20, 2013; Control No. 95/002,309.
Comments by Third-Party Requester to Response to Non-Final Office Action in Inter Partes Reexamination; dated Mar. 11, 2013; Control No. 95/000,690.
Declaration of Anthony John Kinney dated Mar. 6, 2013; Inter Partes Reexamination; Control No. 95/000,690.
Zhang et al, "Effects of Expander Process on the Phospholipids in Soybean Oil", Journal of American Oil Chemist's Society, Oct. 1994, pp. 1145-1148, vol. 71, No. 10.
Notice of Defective Paper; dated Apr. 12, 2013; Control No. 95/002,309.
Corrected Comments by Third-Party Requester to Response to Non-Final Office Action in Inter Partes Reexamination; dated Apr. 23, 2013; Control No. 95/002,309.
Petition to Strike Under 37 CFR 1.182; dated Apr. 17, 2013; Control No. 95/000,690.
First Office Action (India) for PCT/US2007/063643 (WO2007/106728); dated Mar. 28, 2013.
Oilseed heptane extraction procedure from the Cyberlipid "Special Procedures" website. (No date is associated with this website).
Action Closing Prosecution; dated May 30, 2013; Control No. 95/002,028.
Response to Action Closing Prosecution; dated Jun. 28, 2013; Control No. 95/002,028.
About-Definition and More from the Free Merriam-Webster Dictionary. http://www.merriam-webster.com/dictionary/about, accessed Apr. 22, 2013.
Non-Final Office Action; dated May 24, 2013; Control No. 95/002,309.
Petition to Review Under 37 CFR1.181; dated May 14, 2013; Control No. 95/002,309.
Non-Final Office Action (Canada) for CA Patent No. 2,645,148 (WO2007/106728); dated May 7, 2013.
Office Action (Australia) for AU Application No. 2007226680 (WO2007/106728); dated Mar. 19, 2012.
Response to Office Action (Australia) for AU Application No. 2007226680 (WO2007/106728); dated May 2, 2013.
Non-Final Office Action (US) for U.S. Appl. No. 13/669,024; dated Apr. 11, 2013.
Response to Non-Final Office Action; dated Jul. 23, 2013; Control No. 95/002,309.
Response to Inter Partes Reexamination Non-Final Office Action Under 37 C.F.R 1.945 for U.S. Pat. No. 8,057,835, dated Oct. 15, 2012.
2nd Declaration of Toni Voelker, dated Feb. 7, 2013, filed with response to Inter Partes Reexamination of U.S. Pat. No. 7,943,818; Control No. 95/000,690.
Response to Inter Partes Reexamination Non-Final Office Action Under 37 C.F.R 1.945 for U.S. Pat. No. 7,943,818, dated Dec. 7, 2012.
Non-Final Office Action dated Oct. 11, 2012; U.S. Appl. No. 13/295,501.
Response to Non-Final Office Action dated Jan. 10, 2013; U.S. Appl. No. 13/295,501.
Non-Final Office Action dated Feb. 14, 2013; U.S. Appl. No. 13/295,501.
Non-Final Office Action dated Jan. 11, 2012; U.S. Appl. No. 13/080,087.
Response to Non-Final Office Action dated Apr. 10, 2012; U.S. Appl. No. 13/080,087.
Non-Final Office Action dated Jul. 5, 2012; U.S. Appl. No. 13/080,087.
Response to Non-Final Office Action dated Nov. 5, 2012; U.S. Appl. No. 13/080,087.

Final Office Action dated Feb. 22, 2013; U.S. Appl. No. 13/080,087.
Preliminary Amendment dated Nov. 5, 2012; U.S. Appl. No. 13/669,024.
Comments by Third-Party Requester to Response to Non-Final Office Action in inter partes Reexamination; dated Jul. 29, 2013; Control No. 95/002,028.
Comments by Third-Party Requester to Response to Non-Final Office Action in Inter Partes Reexamination; dated Feb. 1, 2013; Control No. 95/002,309.
Extended European Search Report issued in analogous application No. EP 12193422.8 dated Jan. 21, 2013.
Notice of Defective Paper; dated Jul. 31, 2013; Control No. 95/002,309.
Response to the Notice of Defective Paper dated Aug. 16, 2013; Control No. 95/002,309.
Response dated Aug. 21, 2013 from USPTO to Petition to Review Under 37 CFR1.181; filed May 14, 2013; Control No. 95/002,309.
Office Action dated Apr. 29, 2010 for U.S. Appl. No. 12/320,692.
Final Office Action dated Nov. 9, 2010 for U.S. Appl. No. 12/320,692.
Office Action dated May 10, 2012 for U.S. Appl. No. 12/320,692.
Final Office Action dated Jan. 7, 2013 for U.S. Appl. No. 12/320,692.
Office Action dated May 16, 2013 for U.S. Appl. No. 12/320,692.
Kurki et al, "Oilseed Processing for Small-Scale Producers", ATTRA, 2008, pp. 1-16.
Cyberlipid Center/Analysis/Lipid Extraction/Oilseed processing as accessed on Sep. 9, 2013 at the website, <http://www.cyberlipid.org/extract/extr0001.htm>.
Declaration of Toni Voelker dated Nov. 25, 2013; Control No. 95/002309.
Brace et al, "Agronomic and Seed Traits of Soybean Lines with High Oleate Concentration", Crop Science, Mar.-Apr. 2011, pp. 534-541, vol. 51.
Anai et al., "Identification of Corresponding Genes for Three Low-?-Linolenic Acid Mutants and Elucidation of their contribution to Fatty Acid Biosynthesis in Soybean Seed", Plant Science, 2005, pp. 1615-1623. vol. 168.
Bilyeu et al., Plant Genetics Meeting on Mechanisms of Genetic Variation, Oct. 22-26, 2003, Abstract, p. 50, XP009060561.
Bilyeu et al., 10th Biennial Conference of the Cellular and Molecular Biology of the Soybean, 2004.
Bilyeu et al., "Molecular Genetic Resources for Development of 1& Linolenic Acid Soybeans", Crop Science, 2006, p. 1913-1918, vol. 46.
Bilyeu et al., "Novel FAD3 Mutant Allele Combinations Produce Soybeans Containing 1% Linolenic Acid in the Seed Oil", Crop Science, 2011, p. 259-264, vol. 51.
Brummer et al, "Mapping the Fan Locus Controlling Linolenic Acid Content in Soybean Oil", Journal of Heredity, 1995, p. 245-247, vol. 86.
Fehr et al., "Inheritance of Reduced Linolenic Acid Content in Soybean Genotypes A16 and A17", Crop Science, 1992, p. 903-906, vol. 32.
Fehr et al., "Breeding for Modified Fatty Acid Composition in Soybean", Crop Science, 2007, p. S72-S87, vol. 47.
GenBank Accession No. AY204710, May 17, 2005.
GenBank Accession No. AY204711, May 17, 2005.
GenBank Accession No. AY204712, May 17, 2005.
Jourden et al., "Specific Molecular Marker of the Genes Controlling Linolenic Acid Content in Rapeseed", Theoretical Applied Genetics, 1996, p. 512-518, vol. 93.
Knutzon et al., "Modification of *Brassica* Seed Oil by Antisense Expression of a Stearoyl-Acyl Carrier Protein Desaturase Gene", Proceedings of the National Academy of Sciences, 1992, p. 2624-2628. vol. 89.
Liu et al., "Oxidative Stability of Soybean Oils with Altered Fatty Acid Compositions", Journal of the American Oil Chemists Society, 1992, p. 528-532, vol. 69.
McBride, Back-to-Basics Breeding, USDA, Mar. 27, 2000.
O'Brien, Fats and oils: Formulating and processing for applications: 2003. p. 14-15, CRC Press.

(56) References Cited

OTHER PUBLICATIONS

Primomo et al., "Inheritance and Interaction of Low Palmitic and Low Linolenic Soybean", Crop Science, 2002, p. 31-36, vol. 42.
Primomo et al., "Genotype x Environment Interactions, Stability, and Agronomic Performance of Soybean with Altered Fatty Acid Profiles", Crop Science, 2002, p. 37-44, vol. 42.
Rahman et al., "Gentle Relationships of Soybean Mutants for Different Linolenic Acid Contents", Crop Science, 1998, p. 702-706, vol. 38.
Rajcan et al., "Detection of Molecular Markers Associated with Linolenic and Erucic Acid Levels in Spring Rapeseed (*Brassica napur* L.)", Euphytica, 1999, p. 173-181, vol. 105.
Reinprecht et al., "Molecular Basis of the Low Linolenic Acid Trait in Soybean EMS Mutant Line RG10", Plant Breading, 2009, p. 253-258, vol. 128.
Rennie et al., "New Allele at the Fan Locus in the Soybean Line A5", Crop Science, 1991, p. 297-301, vol. 31.
Walker et al., "Reduced-Linolenate Content Associations with Agronomic and Seed Traits of Soybean", Crop Science, 1998, p. 352-355, vol. 38.
Wilcox et al., "Relationships Between the Fan Allele and Agronomic Traits in Soybean", Crop Science, 1993, p. 87-89, vol. 33.
Wilcox et al., "Gene Symbol Assigned for Linolenic Acid Mutant in the Soybean" Journal of Heredity, 1987, p. 410, vol. 78.
Wilson, Essential Fatty Acids and Eicosanoids, 2003, p. 53-55, Yongsheng Huang, Shing Shyong XP049169197.
Yadav et al., "Cloning of Higher Plant ?-3 Fatty Acid Desaturases" Plant Physiology, 1993, p. 467-476, vol. 103.
Asgrow Announces New 2002 Soybean Varieties, Seed Today, 2001.
Asgrow Introduces 15 New Bean Varieties, High Plain Journal; 2003.
Dubois et al, "Fatty Acid Profiles of 80 Vegetable Oils with Regard to Their Nutritional Potential", European Journal of Science and Technology, 2007, pp. 710-732, vol. 109.
Chu, "A Comparative Study of Analytical Methods for Evaluation of Soybean Oil Quality", Journal of the American Oil Chemist's Society, Jun. 1991, pp. 379-384, vol. 68, No. 6.
Buhr, "Ribozyme Termination of RNA Transcripts Down-Regulate Seed Fatty Acid Genes in Transgenic Soybean", Plant Journal, 2002, pp. 155-163, vol. 30, No. 2.
Burton et al., "Registration of 'Soyola' Soybean", Crop Science, Mar.-Apr. 2004, pp. 687-688.
Byrum et al., "Alteration of the Omega-3 Fatty Acid Desaturase Gene is Associated With Reduced Linolenic Acid in the A5 Soybean Genotype", Theoretical and Applied Genetics, 1997, pp. 356-359, vol. 94, Springer-Verlag.
Extended European Search Report for EP Application 07758217.9 dated Apr. 8, 2010.
Fehr et al., "Breeding for Fatty Acid Composition of Soybean Oil", VII World Soybean Research Conference, IV International Soybean Processing and Utilization Conference, Ill Congresso Mundial de Soja (Brazilian Soybean Congress, Proceedings, Feb. 29-Mar. 5, 2004, pp. 815-821.
Hawkins et al., "Characterization of Acyl-ACP Thioesterases of Mangosteen (*Garcinia mangostana*) Seed and High Levels of Stearate Production in Transgenic Canola", The Plant Journal, 1988, pp. 743-752, vol. 13, Issue 6.
International Search Report and Written Opinion for PCT/U52007/063643 dated Oct. 10, 2008.
Jaworski, "Industrial Oils From Transgenic Plants", Current Opinion in Plant Biology, 2003, pp. 178-184, vol. 6.
Kinney et al., "Designer Oils: The High Oleic Acid Soybean", Genetic Modification in the Food Industry, date unknown, pp. 193-213.
Ross et al., "Agronomic and Seed Traits of 1% Linolenate Soybean Genotypes", Crop Science, Mar.-Apr. 2000, pp. 383-386, vol. 40.
Singh, "Metabolic Engineering of New Fatty Acids in Plants", Current Opinion in Plant Biology, 2005, pp. 197-203, vol. 8.
Stoutjesdijk et al., "hpRNA-Mediated Targeting of the Arabidopsis FAD2 Gene Gives Highly Efficient and Stable Silencing", Plant Physiology, Aug. 1, 2002, pp. 1723-1731, vol. 129, American Society of Plant Physiologists, Rockville, MD, US.
Thomas et al., "Size Constraints for Targeting Post-Transcriptional Gene Silencing and for RNA-Directed Methylation in Nicotiana benthamiana Using a Potato Virus X Vector", The Plant Journal, Feb. 1, 2001, pp. 117-425, vol. 25, No. 4, Blackwell Scientific Publications, Oxford, GB.
Wilcox et al., "Inheritance of Low Linolenic Acid Content of the Seed of a Mutant of Glycine Max", Theoretical and Applied Genetics, 1985, pp. 74-78, vol. 71.
Rahman et al., "Combing Ability in Loci for High Oleic and Low Linolenic Acids in Soybean", Crop Science, 2001, vol. 41, pp. 26-29.
Gryson et al., "Detection of DNA During the Refining of Soybean Oil", Journal of the American Oil Chemists' Society, 2002, pp. 171-174, vol. 79, No. 2.
Wen et al., "Qualitative Detection for Genetically Modified Organisms in Edible Oils by PCR", Chinese Oils, 2002, 7 pages, vol. 27, Issue 2 (English translation and Chinese publication included).
Request for Continued Examination filed in U.S. Appl. No. 11/953,108 dated Sep. 5, 2011, application assigned to E.I. du Pont de Nemours and Company, 14 pages.
Declaration of Dr. Anthony John Kinney, dated Jun. 15, 2012 in support of the Booth patent, filed in connection with Reexamination Requests for U.S. Pat. No. 7,790,953, and U.S. Pat. No. 7,943,818.
Toni Voelker, et al., "Variations in the Biosynthesis of Seed-Through Storage Lipids", Annu. Rev. Plant Physiol. Plant Mol. Biol. 2001, 52:335-61.
Ackman, "Flame Ionization Detection Applied to Thin-Layer Chromatography on Coated Quartz Rods", Methods in Enzymology, 1981, p. 205-252, vol. 72.
Bilyeu et al., "Three Microsomal Omega-3 Fatty-acid Desaturase Genes Contribute to Soybean Linolenic Acid Levels", Crop Science, 2003, p. 1833-1838, vol. 43.
Christie, Gas Chromatography and Lipids, 1989 (Reprinted 1990), The Oily Press.
Hermansson et al., "Automated Quantitative Analysis of Complex Lipidomes by Liquid Chromatography/Mass Spectrometry", Anal. Chem., 2005, p. 2166-2175, vol. 77.
Lee et al., "Targeted Lipidomics Using Electron Capture Atmospheric Pressure Chemical Ionization Mass Spectrometry", Rapid Communications in Mass Spectrometry, 2003, p. 2168-2176, vol. 17.
Declaration of Dr. Anthony John Kinney, dated Sep. 11, 2012 in support of prior art references, filed in connection with reexamination request for U.S. Pat. No. 7,943,818.
Request for Inter Partes Reexamination of U.S. Pat. No. 7,943,818 filed by E.I. du Pont de Nemours and Company.
Request for Inter Partes Reexamination of U.S. Pat. No. 7,790,953 filed by E.I. du Pont de Nemours and Company.
Response to Inter Partes Reexamination Non-Final Office Action Under 37 C.F.R 1.945 for U.S. Pat. No. 7,790,953, dated Oct. 15, 2012.
Declaration of Jay M. Harrison, dated Oct. 15, 2012, filed with response to Inter Partes Reexamination of U.S. Pat. No. 7,790,953.
Declaration of Toni Voelker, dated Oct. 15, 2012, filed with response to Inter Partes Reexamination of U.S. Pat. No. 7,790,953.
Decision on Reexamination Request and Non-Final Office Action in Inter Partes Reexamination; dated Nov. 1, 2012; Control No. 95/002,309.
Request for Inter Partes Reexamination; U.S. Pat. No. 8,057,835; dated Sep. 14, 2012; Control No. 95/002,309.
Liu et al., "Soybean Phospholipids", Recent Trends for Enhancing the Diversity and Quality of Soybean Products (Chapter 22), Oct. 2011, pp. 483-500, Published by InTech.
Webster's Ninth New Collegiate Dictionary, p. 1129, 1986.
Declaration of Dr. Anthony John Kinney, dated Sep. 12, 2012 in support of prior art references, filed in connection with reexamination request for U.S. Pat. No. 8,057,835.
Warner et al., Frying Quality and Stability of Low- and Ultra-Low-Linolenic Acid Soybeans Oils, JAOCS, 80 (3):275-280, 2003.

(56) References Cited

OTHER PUBLICATIONS

Asoyia, Innovative Soybean Oil Offers Health, Cooking, and Taste Benefits, News Release, www.asoyia.com, Oct. 14, 2004, p. 1-3.
Health Canada, Novel Food Information, Low Linolenic Soybean (0T96-15) Apr. 2001, p. 1-3.
Iowa State University, About 1% Linolenic Soybean Oil, product brochure, www.notrans.iastate.edu/about.html.
Dow Agrosciences, Natreon Canola Oil, product brochure, www.dowagro.com/natreon/canola/index.htm.
Dow Agrosciences, Natreon Canola Oil, Natreon History, product brochure, www.dowagro.com/natreon/canola/history.htm.
Dow Agrosciences, Natreon Canola Oil, Natreon vs. Other Oils, product brochure, www.dowagro.com/natreon/canola/oils.htm.
Cargill, Odyssey, 95 High Stability Canola Oil, Zero Trans Fat High Stability Oil., product brochure, www.clearvalleyoils.com.
Su et al., Oxidative and Flavor Stabilities of Soybean Oils and Low- and Ultra-Low-Linolenic Acid Composition, JAOCS, 80(2):171-176, 2003.
Asoyia, Ultra Low Lin Soybean Oil, product brochure, www.asoyia.com, Oct. 21, 2004, p. 1-2.
Cargill, Clear Valley, High Oleic Sunflower Oil, Zero Trans Fat Oil. High Oxidative Stability. All Natural, product brochure, www.clearvalleyoils.com.
Cargill, Clear Valley 75, High Oleic Canola Oil, Zero Trans Fat Oil. High Stability. Fresh Flavor. Long Product Shelf Life. Product brochure, www.clearvalleyoils.com.
Cargill, Clear Valley 65, High Oleic Canola Oil, Zero Trans Fat Oil with Exceptional Stability in High Heat Applications. Product brochure, www.clearvalleyoils.com.

* cited by examiner

SOYBEAN SEED AND OIL COMPOSITIONS AND METHODS OF MAKING SAME

CROSS-REFERENCE TO RELATED APPLICATIONS

This application is a divisional of U.S. application Ser. No. 12/882,579, now U.S. Pat. No. 9,480,271, filed Sep. 15, 2010 and incorporated herein by reference in its entirety, which claims the benefit of U.S. Provisional Application No. 61/242,745, filed on Sep. 15, 2009.

STATEMENT REGARDING FEDERALLY SPONSORED RESEARCH OR DEVELOPMENT

Not Applicable.

APPENDIX

Not Applicable.

INCORPORATION OF SEQUENCE LISTING

The sequence listing that is contained in the file named "38-77(54823_A) SEQ LIST", which is 39,716 bytes in size (measured in MS-Windows), created in 10 Mar. 2009 is filed herewith by electronic submission and herein incorporated by reference. This Sequence Listing consists of SEQ ID NOs:1-7.

BACKGROUND OF THE INVENTION

1. Field of the Invention

This invention relates generally to modulating fatty acid profiles of soybean seed through genetic engineering and the resulting soybean oil compositions. Recombinant DNA constructs, soybean plants and seeds, and soybean oil composition with altered fatty acid profile are provided.

2. Related Art

Plant oils are used in a variety of applications. Novel vegetable oil compositions and improved approaches to obtain oil compositions, from synthetic or natural plant sources, are needed. Depending upon the intended oil use, various fatty acid compositions are desired. Plants, especially species which synthesize large amounts of oils in seeds, are an important source of oils both for edible and industrial uses. Seed oils are composed almost entirely of triacylglycerols in which fatty acids are esterified to the three hydroxyl groups of glycerol.

Soybean oil typically contains about 11-17% saturated fatty acids: 8-13% palmitate and 3-4% stearate. See generally Gunstone et al., The Lipid Handbook, Chapman & Hall, London (1994). Soybean oil has been modified by various breeding methods to create benefits for specific markets. However, for the production of most baked goods and coatings there is a need for high solids-containing stable fats. In the past, partially hydrogenated soybean oil was used for this purpose, but with the introduction of trans fatty acid labeling, the desirability of this oil has decreased.

Higher plants synthesize fatty acids via a common metabolic pathway—the fatty acid synthetase (FAS) pathway, which is located in the plastids. β-ketoacyl-ACP synthases are important rate-limiting enzymes in the FAS of plant cells and exist in several versions. β-ketoacyl-ACP synthase I catalyzes chain elongation to palmitoyl-ACP (C16:0), whereas β-ketoacyl-ACP synthase II catalyzes chain elongation to stearoyl-ACP (C18:0). In soybean, the major products of FAS are 16:0-ACP and 18:0-ACP. The desaturation of 18:0-ACP to form 18:1-ACP is catalyzed by a plastid-localized soluble delta-9 desaturase (also referred to as "stearoyl-ACP desaturase"). See Voelker et al., 52 Annu. Rev. Plant Physiol. Plant Mol. Biol. 335-61 (2001).

The products of the plastidial FAS and delta-9 desaturase, 16:0-ACP, 18:0-ACP, and 18:1-ACP, are hydrolyzed by specific thioesterases (FAT). Plant thioesterases can be classified into two gene families based on sequence homology and substrate preference. The first family, FATA, includes long chain acyl-ACP thioesterases having activity primarily on 18:1-ACP. Enzymes of the second family, FATB, commonly utilize 16:0-ACP (palmitoyl-ACP), 18:0-ACP (stearoyl-ACP), and 18:1-ACP (oleoyl-ACP). Such thioesterases have an important role in determining chain length during de novo fatty acid biosynthesis in plants, and thus these enzymes are useful in the provision of various modifications of fatty acyl compositions, particularly with respect to the relative proportions of various fatty acyl groups that are present in seed storage oils.

The products of the FATA and FATB reactions, the free fatty acids, leave the plastids and are converted to their respective acyl-CoA esters. Acyl-CoAs are substrates for the lipid-biosynthesis pathway (Kennedy Pathway), which is located in the endoplasmic reticulum (ER). This pathway is responsible for membrane lipid formation as well as the biosynthesis of triacylglycerols, which constitute the seed oil. In the ER there are additional membrane-bound desaturases, which can further desaturate 18:1 to polyunsaturated fatty acids. A delta-12 desaturase (FAD2) catalyzes the insertion of a double bond into oleic acid (OA) (18:1), forming linoleic acid (LA) (18:2). A delta-15 desaturase (FAD3) catalyzes the insertion of a double bond into 18:2, forming alpha linolenic acid (ALA) (18:3).

Inhibition of the endogenous FAD2 genes through use of transgenes that silence the expression of FAD2 has been shown to confer a desirable oleic acid (18:1) phenotype (i.e. soybean seed comprising about 50% and 75% oleic acid by weight). Transgenes and transgenic plants that provide for inhibition of the endogenous FAD2 gene expression and a desirable oleic phenotype are disclosed in U.S. Pat. No. 7,067,722. In contrast, soybean cultivars that lack FAD2-inhibiting transgenes typically produce seed with oleic acid compositions of less than 20%.

Soybean oil typically contains about 8% ALA (18:3) that renders this oil oxidatively unstable. The levels of ALA in soybean oil can be reduced by hydrogenation to improve both stability and flavor. Unfortunately, hydrogenation results in the production of trans-fatty acids, which increases the risk for coronary heart disease when consumed.

Oleic acid has one double bond, but is still relatively stable at high temperatures, and oils with high levels of OA are suitable for cooking and other processes where heating is required. Recently, increased consumption of high OA oils has been recommended, because OA appears to lower blood levels of low density lipoproteins ("LDLs") without affecting levels of high density lipoproteins ("HDLs"). However, some limitation of OA levels is desirable, because when OA is degraded at high temperatures, it creates negative flavor compounds and diminishes the positive flavors created by the oxidation of LA. Neff et al., JAOCS, 77:1303-1313 (2000); Warner et al., J. Agric. Food Chem. 49:899-905 (2001). It is thus preferable to use oils with OA levels that are 65-85% or less by weight, in order to limit off-flavors in food applications such as frying oil and fried food. Other preferred oils have OA levels that are greater than 55% by weight in order to improve oxidative stability.

SUMMARY OF THE INVENTION

It is in view of the above problems that the present invention was developed. The invention first relates to a non-hydrogenated soybean oil composition comprising an oleic acid content greater than 35%, a stearic acid content greater than 10% and a linolenic acid content of less than about 2% of total seed fatty acids by weight. In other embodiments, the stearic acid content is greater than 17%, 25% and/or 30% of total fatty acids by weight. The invention further comprises a soybean plant capable of producing seed that yields the soybean oil composition above and a seed of the soybean plant comprising the soybean oil described above. In other embodiments, the soybean plant with the above oil composition is transgenic. In certain embodiments, the soybean plant with the above oil composition comprises in its genome a DNA construct comprising a DNA segment expressing a thioesterase with activity on stearoyl acyl ACP. In a further embodiment, the thioesterase is encoded by a FATA gene. In yet another embodiment, the thioesterase is a mangosteen thioesterase. In a further embodiment, the thioesterase gene is a polynucleotide encoding the polypeptide sequence of SEQ ID NO: 1. In certain embodiments, the DNA construct further comprises a first DNA segment expressing a thioesterase with activity on stearoyl acyl ACP and a second DNA segment designed to trigger the suppression of an endogenous FAD2 gene or the construct further comprises a first DNA segment expressing a thioesterase with activity on stearoyl acyl ACP and a second DNA segment designed to trigger the suppression of an endogenous FAD3 gene or the construct further comprises a first DNA segment expressing a thioesterase with activity on stearoyl acyl ACP and a second DNA segment designed to trigger the suppression of endogenous FAD2 and FAD3 genes.

The invention further relates to a soybean oil composition produced from a transgenic soybean seed wherein the soybean oil composition comprises a stearic acid content greater than 10% and a linolenic acid content of less than about 5% of total seed fatty acids by weight. In other embodiments, the stearic acid content is greater than 17%, 25% and/or 30% of total fatty acids by weight. The invention further comprises a transgenic soybean plant capable of producing seed that yield the soybean oil composition immediately above and transgenic seed of the transgenic soybean plant comprising the transgenic soybean oil described immediately above. In certain embodiments, the transgenic soybean plant with the immediately above oil composition comprises a DNA construct comprising a DNA segment expressing a thioesterase with activity on stearoyl acyl ACP. In a further embodiment, the thioesterase is encoded by a FATA gene. In yet another embodiment, the the thioesterase is a mangosteen thioesterase. In a further embodiment, the thioesterase gene is a polynucleotide encoding the polypeptide sequence of SEQ ID NO: 1. In certain embodiments, the DNA construct further comprises a first DNA segment expressing a thioesterase with activity on stearoyl acyl ACP and a second DNA segment designed to trigger the suppression of an endogenous FAD2 gene or the construct further comprises a first DNA segment expressing a thioesterase with activity on stearoyl acyl ACP and a second DNA segment designed to trigger the suppression of an endogenous FAD3 gene or the construct further comprises a first DNA segment expressing a thioesterase with activity on stearoyl acyl ACP and a second DNA segment designed to trigger the suppression of endogenous FAD2 and FAD3 genes. The invention further relates to a soybean oil composition produced from a transgenic soybean seed wherein the soybean oil composition comprises a stearic acid content greater than 20% and a linolenic acid content of less than about 1.7% of total seed fatty acids by weight. The invention further relates to a soybean oil composition produced from a transgenic soybean seed wherein the soybean oil composition comprises a stearic acid content greater than 20% and a linolenic acid content of less than about 2% of total seed fatty acids by weight. The invention further relates to a soybean oil composition produced from a transgenic soybean seed wherein the soybean oil composition comprises a stearic acid content greater than 32% and a linolenic acid content of less than about 5% of total seed fatty acids by weight. The invention further relates to a soybean oil composition produced from a transgenic soybean seed wherein the soybean oil composition comprises a stearic acid content greater than 10% and an oleic acid content of about 39 to 57% of total seed fatty acids by weight. The invention further relates to a soybean oil composition produced from a transgenic soybean seed wherein the soybean oil composition comprises a stearic acid content of 10 to 28%, an oleic acid content of 25-57% and a linolenic acid content of less than about 3% of total seed fatty acids by weight.

This invention also encompasses a method for producing a soybean oilseed crop capable of yielding the soybean oil composition comprising an oleic acid content greater than 35%, a stearic acid content greater than 10% and a linolenic acid content of less than about 2% of total seed fatty acids by weight upon heptane extraction, comprising growing a soybean plant of the invention to maturity under plant growth conditions and harvesting seeds from said plant to form a soybean seed crop. The invention also encompasses a method for producing a soybean oilseed crop capable of yielding the soybean oil composition comprising a stearic acid content greater than 10% and a linolenic acid content of less than about 5% of total seed fatty acids by upon heptane extraction, comprising growing a soybean plant of the invention to maturity under plant growth conditions and harvesting seeds from said plant to form a soybean seed crop.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE INVENTION

Figure 1:
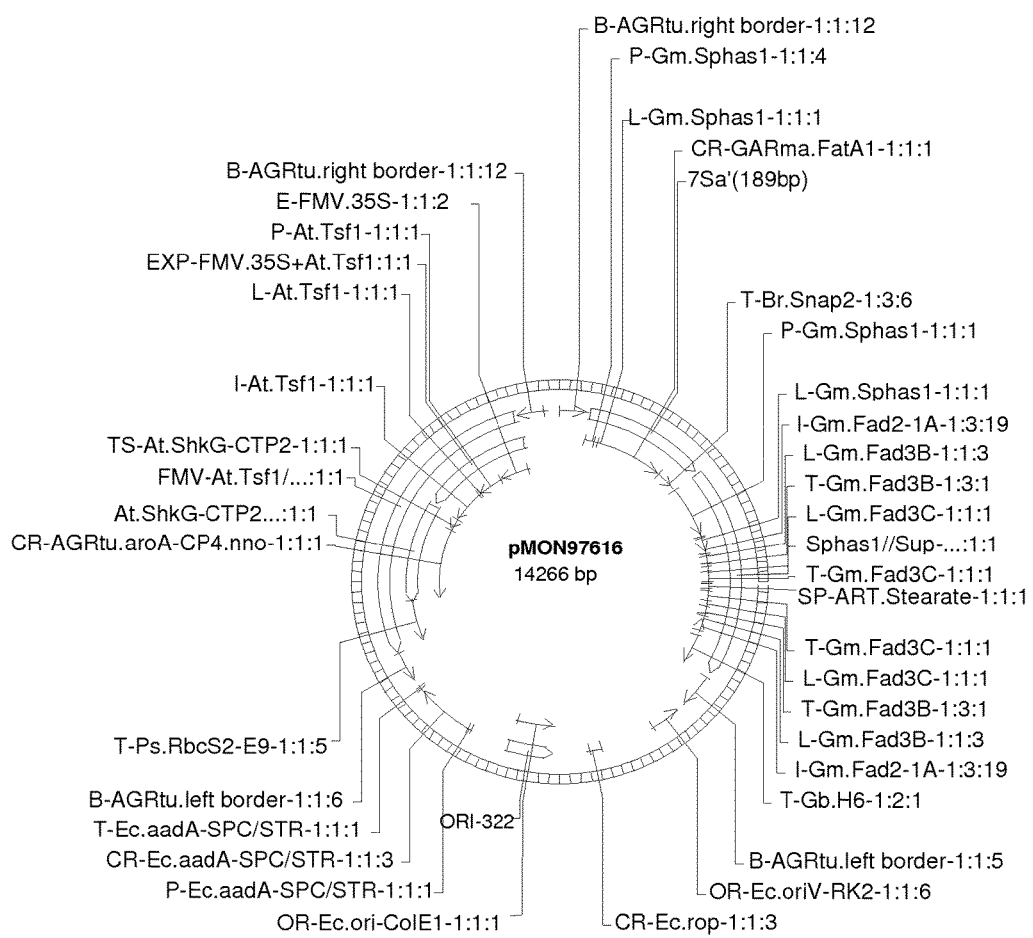
FIG. 1 illustrates the plant vector pMON97616.

Description of the nucleic acid sequences.
SEQ ID NO: 1 is a peptide sequence of a *Garcinia mangostana* FATA.
SEQ ID NO: 2 is a nucleic acid sequence of a *Garcinia mangostana* FATA.

SEQ ID NO: 3 is a nucleic acid sequence of the first T-DNA of pMON97616.

SEQ ID NO: 4 is a nucleic acid sequence of the first T-DNA of pMON97617.

SEQ ID NO: 5 is a nucleic acid sequence of the first T-DNA of pMON97620.

SEQ ID NO: 6 is a nucleic acid sequence of the first T-DNA of pMON97623.

SEQ ID NO: 7 is a nucleic acid sequence of the first T-DNA of pMON97624.

DEFINITIONS

"ACP" refers to an acyl carrier protein moiety.

"Altered seed oil composition" refers to a seed oil composition from a soybean plant of the invention which has altered or modified levels of the fatty acids therein, relative to a typical soybean seed oil.

"Antisense suppression" refers to gene-specific silencing that is induced by the introduction of an antisense RNA molecule.

"Agronomically elite", as used herein, means a genotype that has a culmination of many distinguishable traits such as emergence, vigor, vegetative vigor, disease resistance, seed set, standability and threshability which allows a producer to harvest a product of commercial significance.

"Allele" as used herein, refers to any of one or more alternative forms of a gene locus, all of which alleles relate to a trait or characteristic. In a diploid cell or organism, the two alleles of a given gene occupy corresponding loci on a pair of homologous chromosomes.

"Backcrossing" as used herein, refers to a process in which a breeder repeatedly crosses hybrid progeny, for example a first generation hybrid (F1), back to one of the parents of the hybrid progeny. Backcrossing can be used to introduce one or more single locus conversions from one genetic background into another.

"Coexpression of more than one agent such as an mRNA or protein" refers to the simultaneous expression of an agent in overlapping time frames and in the same cell or tissue as another agent. "Coordinated expression of more than one agent" refers to the coexpression of more than one agent when the production of transcripts and proteins from such agents is carried out utilizing a shared or identical promoter.

"Complement" of a nucleic acid sequence refers to the complement of the sequence along its complete length.

"Cosuppression" is the reduction in expression levels, usually at the level of RNA, of a particular endogenous gene or gene family by the expression of a homologous sense construct that is capable of transcribing mRNA of the same strandedness as the transcript of the endogenous gene. Napoli et al., Plant Cell 2:279-289 (1990); van der Krol et al., Plant Cell 2:291-299 (1990).

A "CP4 EPSPS" or "CP4 5-enolpyruvylshikimate-3-phosphate synthase" gene encodes an enzyme (CP4 EPSPS) capable of conferring a substantial degree of glyphosate resistance upon the plant cell and plants generated therefrom. The CP4 EPSPS sequence may be a CP4 EPSPS sequence derived from *Agrobacterium tumefaciens* sp. CP4 or a variant or synthetic form thereof, as described in U.S. Pat. No. 5,633,435. Representative CP4 EPSPS sequences include, without limitation, those set forth in U.S. Pat. Nos. 5,627,061 and 5,633,435.

"Crossing", as used herein, refers to the mating of two parent plants.

"Cross-pollination", as used herein, refers to fertilization by the union of two gametes from different plants.

"$F_1$" or "F1", as used herein, refers to first generation progeny of the cross of two plants.

"$F_1$ Hybrid" or "F1 Hybrid", as used herein, refers to first generation progeny of the cross of two non-isogenic plants.

"$F_2$" or "F2", as used herein, refers to second generation progeny of the cross of two plants.

"$F_3$" or "F3", as used herein, refers to second generation progeny of the cross of two plants.

"Crude soybean oil" refers to soybean oil that has been extracted from soybean seeds, but has not been refined, processed, or blended, although it may be degummed.

"CTP" refers to a chloroplastic transit peptide, encoded by the "chloroplastic transit peptide coding sequence".

"DNA construct" refers to the heterologous genetic elements operably linked to each other making up a recombinant DNA molecule or segment and may comprise elements that provide expression of a DNA polynucleotide molecule in a host cell and elements that provide maintenance of the construct. A plant expression cassette comprises the operable linkage of genetic elements that when transferred into a plant cell provides expression of a desirable gene product or expression of molecule designed to trigger the suppression of an endogenous gene.

When referring to proteins and nucleic acids herein, "derived" refers to either directly (for example, by looking at the sequence of a known protein or nucleic acid and preparing a protein or nucleic acid having a sequence similar, at least in part, to the sequence of the known protein or nucleic acid) or indirectly (for example, by obtaining a protein or nucleic acid from an organism which is related to a known protein or nucleic acid) obtaining a protein or nucleic acid from a known protein or nucleic acid. Other methods of "deriving" a protein or nucleic acid from a known protein or nucleic acid are known to one of skill in the art.

Double-stranded RNA ("dsRNA") and RNA interference ("RNAi") refer to gene-specific silencing that is induced by the introduction of a construct capable of transcribing an at least partially double-stranded RNA molecule. A "dsRNA molecule" and an "RNAi molecule" both refer to a region of an RNA molecule containing segments with complementary nucleotide sequences and therefore can hybridize with each other and form double-stranded RNA. Such double-stranded RNA molecules are capable, when introduced into a cell or organism, of at least partially reducing the level of an mRNA species present in a cell or a cell of an organism. In addition, the dsRNA can be created after assembly in vivo of appropriate DNA fragments through illegitimate recombination and site-specific recombination as described in International Application No. PCT/US2005/004681, filed on Feb. 11, 2005, which is hereby incorporated by reference in its entirety.

"Exon" refers to the normal sense of the term as meaning a segment of nucleic acid molecules, usually DNA, that encodes part of or all of an expressed protein.

"FAD2" refers to, depending on the context, a gene (FAD2) or encoded protein(FAD2) capable of catalyzing the insertion of a double bond into a fatty acyl moiety at the twelfth position counted from the carboxyl terminus. Italicized capital letters refer to genes and non-italicized capital letters refer to proteins. FAD2 proteins are also referred to as "Δ12 desaturase" or "omega-6 desaturase". The term "FAD2-1" is used to refer to, depending on the context, a FAD2 gene or protein that is naturally expressed in a specific manner in seed tissue, and the term "FAD2-2" is used to refer to, depending on the context, a FAD2 gene or protein that is (a) a different gene from a FAD2-1 gene or protein and (b) is naturally expressed in multiple tissues, including the seed.

A "FAD3", "Δ15 desaturase" or "omega-3 desaturase" gene encodes an enzyme (FAD3) capable of catalyzing the insertion of a double bond into a fatty acyl moiety at the fifteenth position counted from the carboxyl terminus. The terms "FAD3-1, FAD3-A, FAD3-B and FAD3-C" are used to refer to FAD3 gene family members that are naturally expressed in multiple tissues, including the seed.

A "FATA" or "long chain acyl-ACP thioesterase" refers to a gene that encodes an enzyme (FATA) capable of catalyzing the hydrolytic cleavage of the carbon-sulfur thioester bond in the panthothene prosthetic group of acyyl-ACP as its preferred reaction with activity primarily on 18:1-ACP".

"Fatty acid" refers to free fatty acids and/or fatty acyl groups.

"Gene" refers to a nucleic acid sequence that encompasses a 5' promoter region associated with the expression of the gene product, any intron and exon regions and 3' or 5' untranslated regions associated with the expression of the gene product.

"Gene silencing" refers to the suppression of gene expression or down-regulation of gene expression.

A "gene family" is two or more genes in an organism which encode proteins that exhibit similar functional attributes, and a "gene family member" is any gene of the gene family found within the genetic material of the plant, e.g., a "FAD2 gene family member" is any FAD2 gene found within the genetic material of the plant. An example of two members of a gene family are FAD2-1 and FAD2-2. A gene family can be additionally classified by the similarity of the nucleic acid sequences. A gene, FAD2, for example, includes alleles at that locus. Preferably, a gene family member exhibits at least 60%, more preferably at least 70%, more preferably at least 80% nucleic acid sequence identity in the coding sequence portion of the gene.

"Genotype", as used herein, refers to the genetic constitution of a cell or organism.

As used herein, "Heterologous" means not naturally occurring together.

A nucleic acid molecule is said to be "introduced" if it is inserted into a cell or organism as a result of human manipulation, no matter how indirect. Examples of introduced nucleic acid molecules include, but are not limited to, nucleic acids that have been introduced into cells via transformation, transfection, injection, and projection, and those that have been introduced into an organism via methods including, but not limited to, conjugation, endocytosis, and phagocytosis.

"Intron" refers to the normal sense of the term as meaning a segment of nucleic acid molecules, usually DNA, that does not encode part of or all of an expressed protein, and which, in endogenous conditions, is transcribed into RNA molecules, but which is spliced out of the endogenous RNA before the RNA is translated into a protein. An "intron dsRNA molecule" and an "intron RNAi molecule" both refer to a double-stranded RNA molecule capable, when introduced into a cell or organism, of at least partially reducing the level of an mRNA species present in a cell or a cell of an organism where the double-stranded RNA molecule exhibits sufficient identity to an intron of a gene present in the cell or organism to reduce the level of an mRNA containing that intron sequence.

A "low saturate" soybean seed oil composition contains between 3.6 and 8 percent saturated fatty acids by weight of the total fatty acids.

A "low linolenic" oil composition contains less than about 3% linolenic acid by weight of the total fatty acids.

A "mid-oleic soybean seed" is a seed having between 55% and 85% oleic acid by weight of the total fatty acids.

The term "non-coding" refers to sequences of nucleic acid molecules that do not encode part or all of an expressed protein. Non-coding sequences include but are not limited to introns, promoter regions, 3' untranslated regions (3'UTRs), and 5' untranslated regions (5'UTRs).

The term "oil composition" refers to a soybean oil with specified levels of fatty acids.

"Phenotype", as used herein, refers to the detectable characteristics of a cell or organism, which characteristics are the manifestation of gene expression.

A promoter that is "operably linked" to one or more nucleic acid sequences is capable of driving expression of one or more nucleic acid sequences, including multiple coding or non-coding nucleic acid sequences arranged in a polycistronic configuration.

"Physically linked" nucleic acid sequences are nucleic acid sequences that are found on a single nucleic acid molecule. A "plant" includes reference to whole plants, plant organs (e.g., leaves, stems, roots, etc.), seeds, and plant cells and progeny of the same. The term "plant cell" includes, without limitation, seed suspension cultures, embryos, meristematic regions, callus tissue, leaves, roots, shoots, gametophytes, sporophytes, pollen, and microspores. "Plant promoters," include, without limitation, plant viral promoters, promoters derived from plants, and synthetic promoters capable of functioning in a plant cell to promote the expression of an mRNA.

A "polycistronic gene" or "polycistronic mRNA" is any gene or mRNA that contains transcribed nucleic acid sequences which correspond to nucleic acid sequences of more than one gene targeted for suppression. It is understood that such polycistronic genes or mRNAs may contain sequences that correspond to introns, 5'UTRs, 3'UTRs, transit peptide encoding sequences, exons, or combinations thereof, and that a recombinant polycistronic gene or mRNA might, for example without limitation, contain sequences that correspond to one or more UTRs from one gene and one or more introns from a second gene.

As used herein, the term "$R_0$", "R0", "$R_0$ generation" or "R0 generation" refers to a transformed plant obtained by regeneration of a transformed plant cell.

As used herein, the term "$R_1$," "R1", "$R_1$ generation" or "R1 generation" refers to seeds obtained from a selfed transgenic $R_0$ plant. $R_1$ plants are grown from the $R_1$ seeds.

A "seed-specific promoter" refers to a promoter that is active preferentially or exclusively in a seed. "Preferential activity" refers to promoter activity that is substantially greater in the seed than in other tissues, organs or organelles of the plant. "Seed-specific" includes without limitation activity in the aleurone layer, endosperm, and/or embryo of the seed.

"Sense intron suppression" refers to gene silencing that is induced by the introduction of a sense intron or fragment thereof. Sense intron suppression is described, for example by Fillatti in PCT WO 01/14538 A2.

"Simultaneous expression" of more than one agent such as an mRNA or protein refers to the expression of an agent at the same time as another agent. Such expression may only overlap in part and may also occur in different tissue or at different levels.

"Total oil level" refers to the total aggregate amount of fatty acid without regard to the type of fatty acid. As used herein, total oil level does not include the glycerol backbone.

"Transgene" refers to a nucleic acid sequence associated with the expression of a gene introduced into an organism. A transgene includes, but is not limited to, a gene endogenous or a gene not naturally occurring in the organism.

A "transgenic plant" is any plant that stably incorporates a transgene in a manner that facilitates transmission of that transgene from a plant by any sexual or asexual method.

A "zero saturate" soybean seed oil composition contains less than 3.6 percent saturated fatty acids by weight.

A "loss-of-function mutation" is a mutation in the coding sequence of a gene, which causes the function of the gene product, usually a protein, to be either reduced or completely absent. A loss-of-function mutation can, for instance, be caused by the truncation of the gene product because of a frameshift or nonsense mutation. A phenotype associated with an allele with a loss of function mutation can be either recessive or dominant.

A cell or organism can have a family of more than one gene encoding a particular enzyme, and the capital letter that follows the gene terminology (A, B, C) is used to designate the family member, i.e., FAD2-1A is a different gene family member from FAD2-18. Similarly, FAD3-1A, FAD3-18, and FAD3-1C represent distinct members of the FAD3-1 gene family. Loss of function alleles of various genes are represented in lowercase followed by a minus sign (i.e. fad3-1b- and fad3-1c-represent loss of function alleles of the FAD3-1E3 and FAD3-1C genes, respectively).

As used herein, any range set forth is inclusive of the end points of the range unless otherwise stated.

A. Transgenes that decrease the expression of the endogenous soybean FAD2-1 gene Various transgenes that decrease the expression of the endogenous soybean FAD2-1 gene can be used to practice the methods of the invention. By suppressing, at least partially reducing, reducing, substantially reducing, or effectively eliminating the expression of the endogenous FAD2 gene, the amount of FAD2 protein available in a plant cell is decreased, i.e. the steady-state levels of the FAD2 protein are reduced. Thus, a decrease in expression of FAD2 protein in the soybean cell can result in an increased proportion of mono-unsaturated fatty acids such as oleate (C18:1). Soybean plants that contain transgenes that decrease the expression of the endogenous soybean FAD2-1 and produce seed with increased oleic acid are described in U.S. Pat. No. 7,067,722.

Various transgenes that decrease the expression endogenous soybean FAD3 gene can be used to practice the methods of the invention for production of soybean plants with a low alpha linolenic acid phenotype. By suppressing, at least partially reducing, reducing, substantially reducing, or effectively eliminating the expression of the endogenous FAD3 gene, the amount of FAD3 protein available in a plant cell is decreased, i.e. the steady-state levels of the FAD3 protein are reduced. Thus, a decrease of FAD3 can result in an decreased proportion of unsaturated fatty acids such as alpha linolenic acid (18:3).

Various methods for decreasing expression of either: 1) the endogenous soybean FAD3 gene(s) or 2) both the endogenous soybean FAD2-1 and FAD3 gene(s) in soybean plants and seed are contemplated by this invention, including, but not limited to, antisense suppression, co-suppression, ribozymes, combinations of sense and antisense (double-stranded RNAi), promoter silencing, and use of DNA binding proteins such as zinc finger proteins. The general; practice of these methods with respect to various endogenous plant genes is described in WO 98/53083, WO 01/14538, and U.S. Pat. No. 5,759,829. Suppression of gene expression in plants, also known as gene silencing, occurs at both the transcriptional level and post-transcriptional level. Certain of these gene silencing mechanisms are associated with nucleic acid homology at the DNA or RNA level. Such homology refers to similarity in DNA or protein sequences within the same species or among different species. Gene silencing occurs if the DNA sequence introduced to a host cell is sufficiently homologous to an endogenous gene that transcription of the introduced DNA sequence will induce transcriptional or post transcriptional gene silencing of the endogenous gene. To practice this invention, DNA sequences with about 70% identityover the entire length of a DNA sequence of a soybean FAD2-1 or FAD3 coding region or non-coding region, or to a nucleic acid sequence that is complementary to a soybean FAD2-1 or FAD3 coding or non-coding region, have sufficient homology for suppression of steady state expression levels of FAD2-1 or FAD3 when introduced into soybean plants as transgenes. The transgenes of the invention more preferably comprise DNA sequences that are, over their entire length, at least 80% identical; at least 85% identical; at least 90% identical; at least 95% identical; at least 97% identical; at least 98% identical; at least 99% identical; or 100% identical to a soybean FAD2-1 or FAD3 gene coding region or non-coding region, or to a nucleic acid sequence that is complementary to a soybean FAD2-1 or FAD3 gene coding or non-coding region. The DNA sequences with the above indicated levels of identity to the soybean FAD2-1 or FAD3 gene(s) may be coding sequences, intron sequences, 3'UTR sequences, 5'UTR sequences, promoter sequences, other non-coding sequences, or any combination of the foregoing. The intron may be located between exons, or located within a 5' or 3' UTR of a plant gene. The coding sequence is preferably a fraction of a protein encoding frame that does not encode a protein with FAD2 or FAD3 enzymatic activity. However, it is recognized that in certain instances, such as in cosuppression, DNA sequences that encode an enzymatically active FAD2 or FAD3 protein can be used to decrease expression of the endogenous soybean FAD2-1 or FAD3 gene(s).

It is also understood that DNA sequences with the above indicated levels of identity to the soybean FAD2-1 gene that are useful in the methods of this invention can be derived from any soybean FAD2 gene, the soybean FAD2-1A gene, the soybean FAD2-1A intron, soybean FAD2-1E3 intron, the soybean FAD2-2 gene, alleles of the soybean FAD2-1 gene, alleles of the soybean FAD2-2 gene, and from FAD2 genes derived from other leguminous plants such as *Medicago* sp., *Pisum* sp., *Vicia* sp., *Phaseolus* sp., and *Pisum* sp. DNA sequence with the indicated levels of identity to the soybean FAD2-1 sequence can be derived from multiple sources. DNA sequences with the indicated levels of sequence identity can also be obtained synthetically.

In the methods of this invention, transgenes specifically designed to produce double-stranded RNA (dsRNA) molecules with homology to the FAD2-1 gene can also induce FAD2-1 sequence-specific silencing and be used to decrease expression of the endogenous soybean FAD2-1 gene. The sense strand sequences of the dsRNA can be separated from the antisense sequences by a spacer sequence, preferably one that promotes the formation of a dsRNA molecule. Examples of such spacer sequences include those set forth in Wesley et al., Plant J., 27(6):581-90 (2001), and Hamilton et al., Plant J., 15:737-746 (1988). In a preferred aspect, the spacer sequence is capable of forming a hairpin structure as illustrated in Wesley et al., supra. Particularly preferred spacer sequences in this context are plant introns or parts thereof. A particularly preferred plant intron is a spliceable intron. Spliceable introns include, but are not limited to, an intron selected from the group consisting of PDK intron, FAD3-1A or FAD3-1E3 intron #5, FAD3 intron #1, FAD3 intron #3A, FAD3 intron #3B, FAD3 intron #3C, FAD3 intron #4, FAD3 intron #5, FAD2 intron #1, and FAD2-2 intron. The sense-oriented, non-coding molecules may be, optionally separated from the corresponding antisense-oriented molecules by a spacer segment of DNA. The spacer segment can be a gene fragment or artificial DNA. The spacer segment can be short to facilitate forming hairpin dsRNA or long to facilitate dsRNA without a hairpin structure. The spacer can be provided by extending the length of one of the sense or antisense molecules as disclosed in US 2005/0176670 A1. Alternatively, a right-border-right-border ("RB-RB") sequence can be created after insertion into the plant genome as disclosed in U.S. Patent Application 2005/0183170.

The transgenes of the invention will typically include a promoter functional in a plant cell, or a plant promoter, that is operably linked to an aforementioned DNA sequence that decreases expression of an endogenous soybean FAD2-1 or FAD3 gene. Design of such a vector is generally within the skill of the art (See, e.g., Plant Molecular Biology: A Laboratory Manual, Clark (ed.), Springer, New York (1997)). However, it is recognized that constructs or vectors may also contain a promoterless gene that may utilize an endogenous promoter upon insertion. A number of promoters that are active in plant cells have been described in the literature such as the CaMV 35S and FMV promoters. Enhanced or duplicated versions of the CaMV 35S and FMV 35S promoters can also be used to express an aforementioned DNA sequence that decreases expression of an endogenous FAD2-1 gene (Odell et al., Nature 313: 810-812 (1985); U.S. Pat. No. 5,378,619). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436. In addition, a tissue specific enhancer can be used with a basal plant promoter. Basal promoters typically comprise a "TATA" box and an mRNA cap site but lack enhancer elements required for high levels of expression.

Particularly preferred promoters for use in the transgenes of the instant invention are promoters that express a DNA sequence that decreases expression of an endogenous soybean FAD2-1 or FAD3 gene or that expresses a FATA gene in seeds or fruits. Indeed, in a preferred embodiment, the promoter used is a seed-specific promoter. Examples of such seed-specific promoters include the 5' regulatory regions from such genes as napin (Kridl et al., Seed Sci. Res. 1:209-219 (1991)), phaseolin, stearoyl-ACP desaturase, 7Sα, 7Sα' (Chen et al., Proc. Natl. Acad. Sci., 83:8560-8564 (1986)), USP, arcelin, oleate 12-hydroxylase from *Lesquerella fendleri* (Broun et al., Plant J.13: 201-210 (1998)) and oleosin. Preferred promoters for expression in the seed are 7Sα, 7Sα', napin, and FAD2-1A promoters.

Constructs or vectors will also typically include a 3' transcriptional terminator or 3' polyadenylation signal that is operably linked to an aforementioned DNA sequence that decreases expression of an endogenous soybean FAD2-1 or FAD3 gene or that expresses a FATA gene. The transcriptional termination signal can be any transcriptional termination signal functional in a plant, or any plant transcriptional termination signal. Preferred transcriptional termination signals include, but are not limited to, a pea Rubisco E9 3' sequence, a *Brassica napin* 3' sequence, a tml 3' sequence, and an *Agrobacterium* tumor-inducing (Ti) plasmid nopaline synthase (NOS) gene 3' sequence. It is understood that this group of exemplary polyadenylation regions is non-limiting and that one skilled in the art could employ other polyadenylation regions that are not explicitly cited here in the practice of this invention.

Finally, it is also recognized that transgenes of the invention can be inserted in plant transformation vectors that also comprise genes that encode selectable or scoreable markers. The selectable marker gene can be a gene encoding a neomycin phosphotransferase protein, a phosphinothricin acetyltransferase protein, a glyphosate resistant 5-enol-pyruvylshikimate-3-phosphate synthase (EPSPS) protein, a hygromycin phosphotransferase protein, a dihydropteroate synthase protein, a sulfonylurea insensitive acetolactate synthase protein, an atrazine insensitive Q protein, a nitrilase protein capable of degrading bromoxynil, a dehalogenase protein capable of degrading dalapon, a 2,4-dichlorophenoxyacetate monoxygenase protein, a methotrexate insensitive dihydrofolate reductase protein, and an aminoethylcysteine insensitive octopine synthase protein. The corresponding selective agents used in conjunction with each gene can be: neomycin (for neomycin phosphotransferase protein selection), phosphinotricin (for phosphinothricin acetyltransferase protein selection), glyphosate (for glyphosate resistant 5-enol-pyruvylshikimate-3-phosphate synthase (EPSPS) protein selection), hygromycin (for hygromycin phosphotransferase protein selection), sulfadiazine (for a dihydropteroate synthase protein selection), chlorsulfuron (for a sulfonylurea insensitive acetolactate synthase protein selection), atrazine (for an atrazine insensitive Q protein selection), bromoxinyl (for a nitrilase protein selection), dalapon (for a dehalogenase protein selection), 2,4-dichlorophenoxyacetic acid (for a 2,4-dichlorophenoxyacetate monoxygenase protein selection), methotrexate (for a methotrexate insensitive dihydrofolate reductase protein selection), or aminoethylcysteine (for an aminoethylcysteine insensitive octopine synthase protein selection). A preferred selectable marker gene is a CP4 EPSPS gene that confers resistance to the herbicide glyphosate. The scoreable marker gene can be a gene encoding a beta-glucuronidase protein, a green fluorescent protein, a yellow fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein or a chloramphenicol acetyl transferase protein.

The above-described nucleic acid molecules are embodiments which achieve the objects, features and advantages of the present invention. It is not intended that the present invention be limited to the illustrated embodiments. The arrangement of the sequences in the first and second sets of DNA sequences within the nucleic acid molecule is not limited to the illustrated and described arrangements, and may be altered in any manner suitable for achieving the objects, features and advantages of the present invention as described herein and illustrated in the accompanying drawings.

Transgenic Organisms, and Methods for Producing Same

Any of the nucleic acid molecules and constructs of the invention may be introduced into a soybean plant or plant cell in a permanent or transient manner. Methods and technology for introduction of DNA into soybean plant cells are well known to those of skill in the art, and virtually any method by which nucleic acid molecules may be introduced into a cell is suitable for use in the present invention. Non-limiting examples of suitable methods include: chemical methods; physical methods such as microinjection, electroporation, the gene gun, microprojectile bombardment, and vacuum infiltration; viral vectors; and receptor-mediated mechanisms. Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

Agrobacterium-mediated transfer is a widely applicable system for introducing genes into plant cells. See, e.g., Fraley et al., Bio/Technology 3:629-635 (1985); Rogers et al., Methods Enzymol. 153:253-277 (1987). The region of DNA to be transferred is defined by the border sequences and intervening DNA is usually inserted into the plant genome. Spielmann et al., Mol. Gen. Genet. 205:34 (1986). Modern Agrobacterium transformation vectors are capable of replication in E. coli as well as Agrobacterium, allowing for convenient manipulations. Klee et al., In: Plant DNA Infectious Agents, Hohn and Schell (eds.), Springer-Verlag, New York, pp. 179-203 (1985). Agrobacterium-mediated transformation of soybean is specifically described in U.S. Pat. No. 7,002,058.

Transgenic plants are typically obtained by linking the gene of interest to a selectable marker gene, introducing the linked transgenes into a plant cell, a plant tissue or a plant by any one of the methods described above, and regenerating or otherwise recovering the transgenic plant under conditions requiring expression of said selectable marker gene for plant growth. Exemplary selectable marker genes and the corresponding selective agents have been described in preceding sections of this description of the invention.

Transgenic plants can also be obtained by linking a gene of interest to a scoreable marker gene, introducing the linked transgenes into a plant cell by any one of the methods described above, and regenerating the transgenic plants from transformed plant cells that test positive for expression of the scoreable marker gene. Exemplary scoreable marker genes have been described in preceding sections of this description of the invention.

The regeneration, development and cultivation of plants from single plant protoplast transformants or from various transformed explants is well known in the art. See generally, Maliga et al., Methods in Plant Molecular Biology, Cold Spring Harbor Press (1995); Weissbach and Weissbach, In: Methods for Plant Molecular Biology, Academic Press, San Diego, Calif. (1988). Plants of the present invention can be part of or generated from a breeding program, and may also be reproduced using apomixis. Methods for the production of apomictic plants are known in the art. See, e.g., U.S. Pat. No. 5,811,636.

It is not intended that the present invention be limited to the illustrated embodiments.

Crosses of Soybean Plants Containing Transgenes

In addition to direct transformation of a particular plant genotype with a construct prepared according to the current invention, transgenic plants may be made by crossing a plant having a selected DNA of the invention to a second plant lacking the DNA. A selected DNA construct or constructs that yield a high stearate/low linolenic acid/increased oleic acid phenotype can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes or alleles relative to a starting plant line, as disclosed herein, is defined as the techniques that result in a particular sequence being introduced into a plant line by crossing a starting line with a donor plant line that comprises a transgene or allele of the invention. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

Backcrossing is herein defined as the process including the steps of: (a) crossing a plant of a first genotype containing a desired gene, DNA sequence or element to a plant of a second genotype lacking said desired gene, DNA sequence or element; (b) selecting one or more progeny plant containing the desired gene, DNA sequence or element; (c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

Products of the Present Invention

The plants of the present invention may be used in whole or in part. Preferred plant parts include reproductive or storage parts. The term "plant parts" as used herein includes, without limitation, seed, endosperm, ovule, pollen, roots, tubers, stems, leaves, stalks, fruit, berries, nuts, bark, pods, seeds and flowers. In a particularly preferred embodiment of the present invention, the plant part is a seed.

Any of the plants or parts thereof of the present invention may be processed to produce a feed, meal, protein, or oil preparation. In a preferred embodiment of the present invention can be a plant of the present invention having an oil with a fatty acid composition of the present invention. A particularly preferred plant part for this purpose is a seed. In a preferred embodiment the feed, meal, protein or oil preparation is designed for livestock animals, fish or humans, or any combination. Methods to produce feed, meal, protein and oil preparations are known in the art. See, e.g., U.S. Pat. Nos. 4,957,748, 5,100,679, 5,219,596, 5,936,069, 6,005,076, 6,146,669, and 6,156,227. In a preferred embodiment, the protein preparation is a high protein preparation. Such a high protein preparation preferably has a protein content of greater than 5% w/v, more preferably 10% w/v, and even more preferably 15% w/v.

In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment the oil preparation is a liquid and of a volume greater than 1, 5, 10 or 50 liters. The present invention provides for oil produced from plants of the present invention or generated by a method of the present invention. Such oil may exhibit enhanced oxidative stability. Also, such oil may be a minor or major component of any resultant product.

Moreover, such oil may be blended with other oils. In a preferred embodiment, the oil produced from plants of the present invention or generated by a method of the present invention constitutes greater than 0.5%, 1%, 5%, 10%, 25%, 50%, 75% or 90% by volume or weight of the oil component of any product. In another embodiment, the oil preparation may be blended and can constitute greater than 10%, 25%, 35%, 50% or 75% of the blend by volume. Oil produced from a plant of the present invention can be admixed with one or more organic solvents or petroleum distillates.

Seeds of the plants may be placed in a container. As used herein, a container is any object capable of holding such seeds. A container preferably contains greater than about 500, 1,000, 5,000, or 25,000 seeds where at least about 10%, 25%, 50%, 75% or 100% of the seeds are derived from a plant of the present invention. The present invention also provides a container of over about 10,000, more preferably about 20,000, and even more preferably about 40,000 seeds where over about 10%, more preferably about 25%, more preferably 50% and even more preferably about 75% or 90% of the seeds are seeds derived from a plant of the present invention. The present invention also provides a container of over about 10 kg, more preferably about 25 kg, and even more preferably about 50 kg seeds where over about 10%, more preferably about 25%, more preferably about 50% and even more preferably about 75% or 90% of the seeds are seeds derived from a plant of the present invention.

Soybean seeds produced by the methods of the invention can comprise various oil compositions. An oil produced by soybean seeds produced by the methods of the invention are referred to below as an "oil of the present invention".

An oil of the present invention has a high stearate/low linolenic acid/increased oleic acid composition. In other embodiments, a transgenic oil of the present invention has increased stearate levels and reduced linolenic acid levels. The percentages of fatty acid content, or fatty acid levels, used herein refer to percentages by weight.

In a first embodiment, a non-hydrogenated oil of the present invention has an oil composition that comprises greater than 35% oleic acid, greater than 10% stearate and less than 2% linolenic acid. In other embodiments, the stearic acid content is greater than 17%, 25% and/or 30% of total fatty acids by weight.

In a second embodiment, a soybean oil produced from a transgenic soybean seed of the present invention has an oil composition that is greater than 10% stearate and less than 5% linolenic acid of total fatty acids by weight.

In a third embodiment, a soybean oil produced from a transgenic soybean seed of the present invention has an oil composition that is greater than 20% stearate and less than 1.7% linolenic acid of total fatty acids by weight.

In a fourth embodiment, a soybean oil produced from a transgenic soybean seed produced from a transgenic soybean seed I of the present invention has an oil composition that is greater than 30% stearate and less than 2% linolenic acid of total fatty acids by weight.

In a fifth embodiment, a soybean oil produced from a transgenic soybean seed of the present invention has an oil composition that is greater than 32% stearate and less than 5% linolenic acid of total fatty acids by weight.

In a sixth embodiment, a soybean oil produced from a transgenic soybean seed of the present invention has an oil composition that is greater than 10% stearate and between 39 and 57% oleic acid of total fatty acids by weight.

In a seventh embodiment, a soybean oil produced from a transgenic soybean seed of the present invention has an oil composition that is between 10 and 28% stearate, between 25 and 57% oleic acid and less than 3% linolenic acid of total fatty acids by weight.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Transformation of Soybean A3525 with pMON97616, pMON97617, pMON97620, pMON97623 and pMON97624, and Resultant Phenotypes.

Part I: Vector Descriptions pMON97616

Transgenic soybean plants were generated by an *Agrobacterium*-mediated transformation of soybean cells with the plasmid pMON97616 (FIG. 1). This binary plant transformation vector contains two plant transformation cassettes or T-DNAs. Each T-DNA is flanked by right border and left border sequences at the 5' and 3' ends of the transformation cassette, respectively. The first T-DNA (SEQ ID NO: 3) is used for the expression of an inverted repeat designed to trigger the RNAi based suppression of endogenous FAD2 and FAD3 genes and also for the expression of the FATA gene from *Garcinia mangostana* (SEQ ID NO: 2). The first T-DNA contains two expression cassettes and is organized as follows: the first cassette is comprised of the nopaline RB sequence (basepairs (bp) 1-357), followed by a promoter from the *Glycine max* 7S alpha prime subunit of the beta-conglycinin gene (bp 419-620), which is upstream of the FATA gene from *Garcinia mangostana* (bp 632-1690), which is upstream of the 3' UTR (bp 1696-2008) of the *Brassica rapa* napin gene . The second cassette on the T-DNA begins with the promoter (bp 2058-2885) from the *Glycine max* 7S alpha prime subunit of beta-conglycinin gene, followed by an inverted repeat (bp 2932-4407) containing 221 bp of the FAD2 intron and the 5' and 3' UTRs from two family members of the FAD3 gene family, which is upstream of the 3' UTR of the *Gossypium barbadense* (bp 4451-4886) Sea island cotton H6 gene, which is upstream of the octopine LB sequence (bp 4946-5387). The $2^{nd}$ T-DNA contains the gene cassette conferring glyphosate resistance used as the transformation selectable marker.

pMON97617

Figure 2:
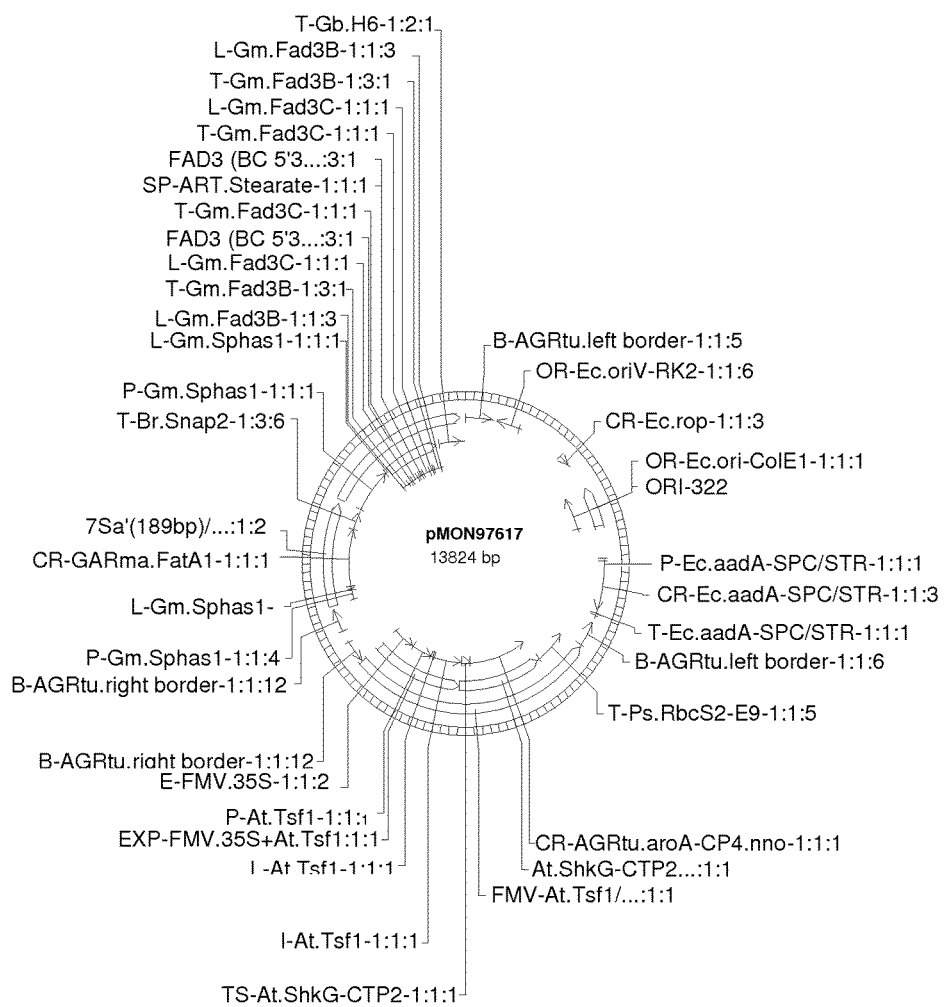
FIG. 2 illustrates the plant vector pMON97617.

Transgenic soybean plants were generated by an *Agrobacterium*-mediated transformation of soybean cells with the plasmid pMON97617 (FIG. 2). This binary plant transformation vector contains two plant transformation cassettes or T-DNAs. Each T-DNA is flanked by right border and left border sequences at the 5' and 3' ends of the transformation cassette, respectively. The first T-DNA (SEQ ID NO: 4) is used for the expression of an inverted repeat designed to trigger the RNAi based suppression of endogenous FAD3 genes and also for the expression of the FATA gene from *Garcinia mangostana*. The first T-DNA contains two expression cassettes and is organized as follows: the first cassette is comprised of the nopaline RB sequence (bp 1-357), followed by a promoter from the *Glycine max* 7S alpha prime subunit of the beta-conglycinin gene (bp 419-620), which is upstream of the FATA gene from *Garcinia mangostana* (bp 632-1690), which is upstream of the 3' UTR (bp 1696-2008) of the *Brassica rapa* napin gene. The second cassette on the T-DNA begins with the promoter (bp 2058-2898) from the *Glycine max* 7S alpha prime subunit of beta-conglycinin gene, followed by an inverted repeat (bp 2932-3965) containing the 5' and 3' UTRs from two family members of the FAD3 gene family, which is upstream of the 3' UTR (bp 4009-4444) of the *Gossypium barbadense* (Sea island cotton) H6 gene, which is upstream of the octopine LB sequence (bp 4504-4945). The $2^{nd}$ T-DNA contains the gene cassette conferring glyphosate resistance used as the transformation selectable marker.

pMON97620

Figure 3:
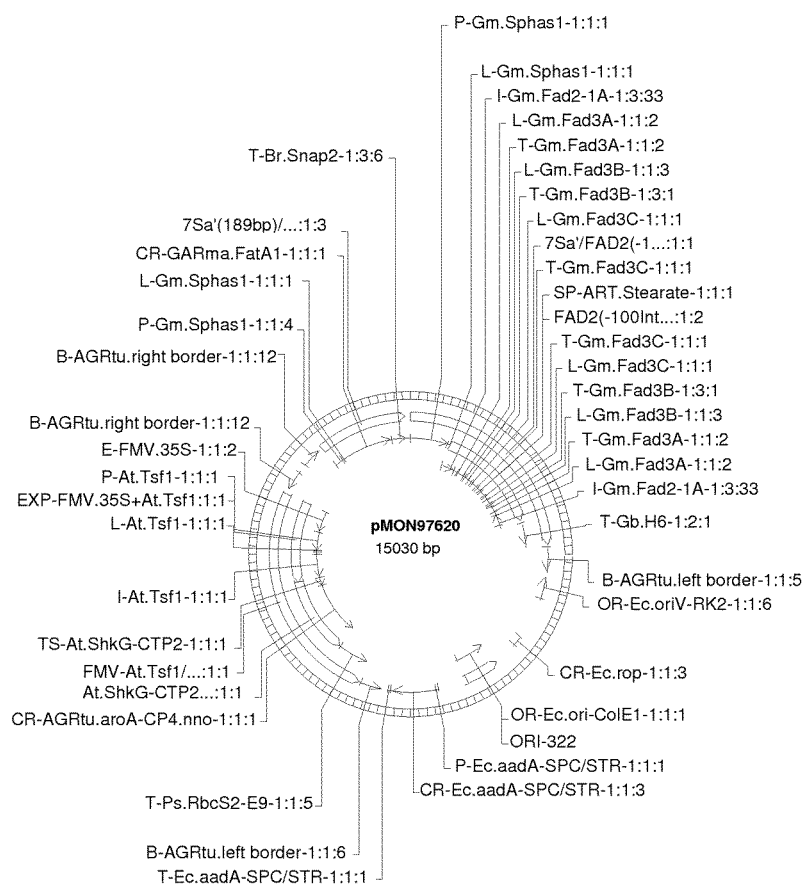
FIG. 3 illustrates the plant vector pMON97620.

Transgenic soybean plants were generated by an *Agrobacterium*-mediated transformation of soybean cells with the plasmid pMON97620 (FIG. 3). This binary plant transformation vector contains two plant transformation cassettes or T-DNAs. Each T-DNA is flanked by right border and left border sequences at the 5' and 3' ends of the transformation cassette, respectively. The first T-DNA (SEQ ID NO: 5) is used for the expression of an inverted repeat designed to trigger the RNAi based suppression of endogenous endogenous FAD2 and FAD3 and also for the expression of the FATA gene from *Garcinia mangostana*. The first T-DNA contains two expression cassettes and is organized as follows: the first cassette is comprised of the nopaline RB sequence (bp 1-357), followed by a promoter (bp 419-620) from the *Glycine max* 7S alpha prime subunit of the beta-conglycinin gene, which is upstream of the FATA gene from *Garcinia mangostana* (bp 632-1690) which is upstream of the 3' UTR (bp 1696-2008) of the *Brassica rapa* napin gene. The second cassette on the T-DNA begins with the promoter (bp 2058-2898) from the *Glycine max* 7S alpha prime subunit of beta-conglycinin gene, followed by an inverted repeat (bp 2932-5171) containing 321 by of the FAD2 intron, and the 5' and 3' UTRs from three family members of the FAD3 gene family, which is upstream of the 3' UTR (bp 5215-5650) of the *Gossypium barbadense* (Sea island cotton) H6 gene, which is upstream of the octopine LB sequence (bp 5710-6151). The $2^{nd}$ T-DNA contains the gene cassette conferring glyphosate resistance used as the transformation selectable marker pMON97623

Figure 4:
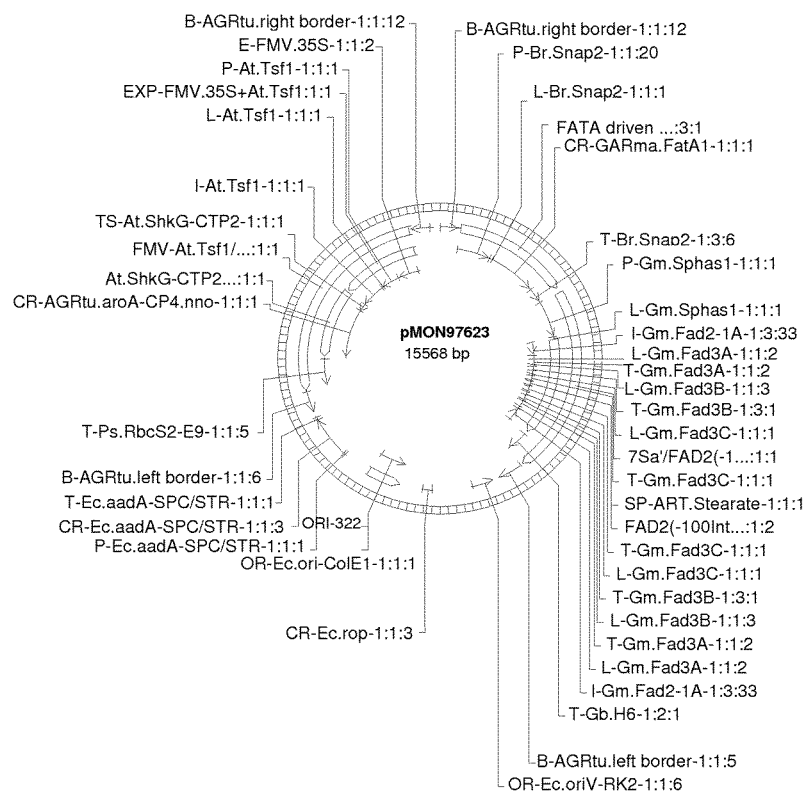
FIG. 4 illustrates the plant vector pMON97623.

Transgenic soybean plants were generated by an *Agrobacterium*-mediated transformation of soybean cells with the plasmid pMON97623 (FIG. 4). This binary plant transformation vector contains two plant transformation cassettes or T-DNAs. Each T-DNA is flanked by right border and left border sequences at the 5' and 3' ends of the transformation cassette, respectively. The first T-DNA (SEQ ID NO: 6) is used for the expression of an inverted repeat designed to trigger the RNAi based suppression of endogenous FAD2 and FAD3 and also for the expression of the FATA gene from *Garcinia mangostana*. The first T-DNA contains two expression cassettes and is organized as follows: the first cassette is comprised of the nopaline RB sequence (bp 1-357), followed by the promoter region (bp 403-1150) from the *Brassica rapa* napin gene, which is upstream of the FATA gene from *Garcinia mangostana* (bp 1170-2228), which is upstream of the 3' UTR (bp 2234-2546) of the *Brassica rapa* napin gene. The second cassette on the T-DNA begins with the promoter (bp 2596-3436) from the *Glycine max* 7S alpha prime subunit of beta-conglycinin gene, followed by an inverted repeat (bp 3470-5709) containing 321 bp of the FAD2 intron, and the 5' and 3' UTRs from three family members of the FAD3 gene family, which is upstream of the 3' UTR (bp 5753-6188) of the *Gossypium barbadense* (Sea island cotton) H6 gene, which is upstream of the octopine LB sequence. The $2^{nd}$ T-DNA contains the gene cassette conferring glyphosate resistance used as the transformation selectable marker pMON97624

Figure 5:
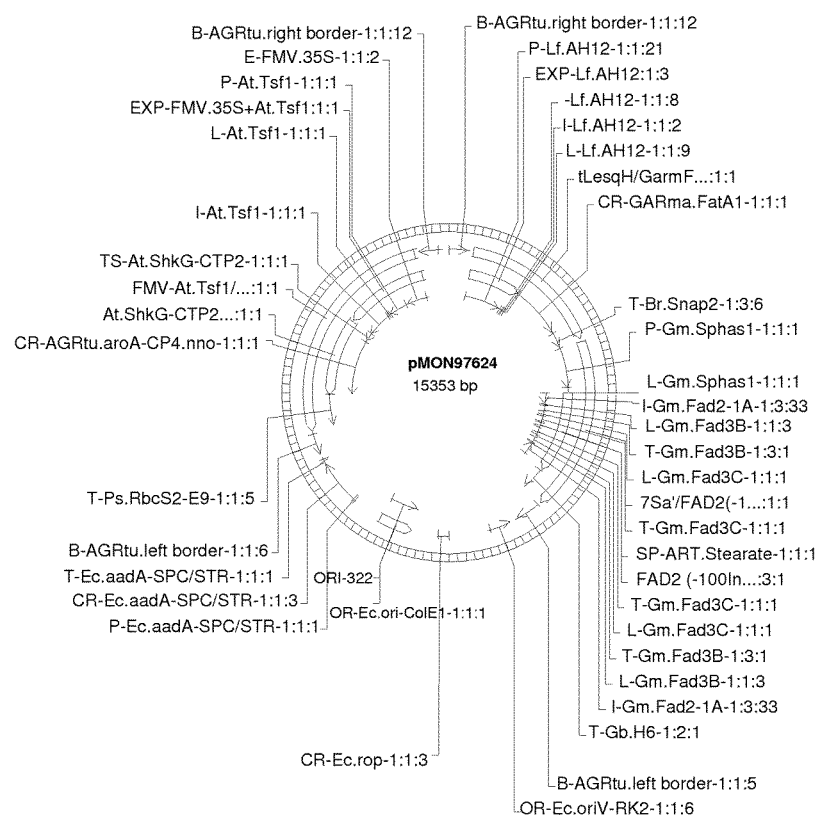
FIG. 5 illustrates the plant vector pMON97624.

Transgenic soybean plants were generated by an *Agrobacterium*-mediated transformation of soybean cells with the plasmid pMON97624 (FIG. 5). This binary plant transformation vector contains two plant transformation cassettes or T-DNAs. Each T-DNA is flanked by right border and left border sequences at the 5' and 3' ends of the transformation cassette, respectively. The first T-DNA (SEQ ID NO: 7) is used for the expression of an inverted repeat designed to trigger the RNAi based suppression of endogenous FAD2 and FAD3 and also for the expression of the FATA gene from Garcinia mangostana. The first T-DNA contains two expression cassettes and is organized as follows: the first cassette is comprised of the nopaline RB sequence (bp 1-357), followed by the promoter region (bp 421-1507) of the *Lesquerella fendleri* oleate desaturase gene AH12, which is upstream of the FATA gene from *Garcinia mangostana* (bp 1519-2577), which is upstream of the 3' UTR (bp 2583-2895) of the *Brassica rapa* napin gene. The second cassette on the T-DNA begins with the promoter (bp 2945-3785) from the *Glycine max* 7S alpha prime subunit of beta-conglycinin gene, followed by an inverted repeat (bp 3819-5494) containing 321 by of the FAD2 intron, and the 5' and 3' UTRs from three family members of the FAD3 gene family, which is upstream of the 3' UTR (bp 5538-5937) of the *Gossypium barbadense* (Sea island cotton) H6 gene, which is upstream of the octopine LB sequence (bp 6033-6474). The $2^{nd}$ T-DNA contains the gene cassette conferring glyphosate resistance used as the transformation selectable marker Part II: Event Selection Explants transformed with pMON97616, pMON97617, pMON97620, pMON97623 and pMON97624 were obtained via *Agrobacterium tumefaciens*-mediated transformation. Plants were regenerated from transformed tissue. 155 R0 transformation events were carried forward after testing for 1-2 copies of the H6 UTR fragment using Invader$^R$ (Third Wave Technologies, Inc., Madison, Wis.). These events were self-pollinated to generate R1 seed. The fatty acid compositions of the R1 seeds were determined by FAME-GC analysis. Pooled samples were ground to a fine powder and lipids were extracted with heptane. The supernatant was transferred in a glass vial and the heptane was evaporated with a flow of dry nitrogen gas at 80° C. An aliquot of the extracted soybean oil (8 mg) was transesterified with sodium methoxide. Resultant fatty acid methyl esters (FAMEs) were separated by capillary gas chromatography and detected by flame ionization detector. The column was a Supelcowax™ 10 with dimensions of 15 m×0.25 mm×0.25 µm film thickness (Sigma-Aldrich, St. Louis, Mo.). An injection volume of 1 µl was used with a split ratio of 100:1. Peaks were identified based on their relative retention time compared to a FAME reference mixture. The resultant relative percent compositions of the major fatty acid components are reported (Table 1). Since the R1 seed are segregating for the insertion, six individual seed were analyzed for each event to look at segregation and the single seed with the highest stearate level was used as an early estimate of the homozygous phenotype.

TABLE 1

Fatty Acid Composition of R1 Seeds

| Event | Construct | 16:0 | 18:0 | 18:1 | 18:2 | 18:3 |
|---|---|---|---|---|---|---|
| GM_A433185 | pMON97617 | 7.7 | 47.56 | 5.85 | 32.65 | 3.66 |
| GM_A446735 | pMON97616 | 7.52 | 46.93 | 26.4 | 14.62 | 1.22 |
| GM_A435769 | pMON97620 | 7.43 | 46.92 | 30.61 | 10.59 | 0.87 |
| GM_A435767 | pMON97620 | 5.66 | 45.46 | 38.66 | 6.53 | 0.73 |
| GM_A446764 | pMON97616 | 6.23 | 43.24 | 6.89 | 33.78 | 7.28 |
| GM_A435982 | pMON97620 | 7.05 | 42.36 | 37.59 | 8.97 | 0.82 |
| GM_A446714 | pMON97616 | 6.44 | 42.15 | 23.98 | 23.25 | 1.78 |
| GM_A435979 | pMON97620 | 5.6 | 41.92 | 39.17 | 9.58 | 0.77 |
| GM_A433338 | pMON97617 | 7.26 | 38.97 | 9.01 | 40.72 | 1.55 |
| GM_A446749 | pMON97616 | 5.05 | 38.01 | 40.76 | 13.13 | 1.14 |
| GM_A432204 | pMON97624 | 6.3 | 38.01 | 9.59 | 36.24 | 7.59 |
| GM_A446724 | pMON97616 | 4.93 | 38 | 43.6 | 9.89 | 0.87 |
| GM_A436393 | pMON97623 | 5.78 | 37.5 | 44.49 | 8.59 | 0.68 |
| GM_A435525 | pMON97620 | 6.63 | 35.82 | 8.77 | 37.77 | 9.26 |
| GM_A436016 | pMON97620 | 5.58 | 35.56 | 36.68 | 18.34 | 1.01 |
| GM_A436608 | pMON97623 | 4.98 | 34.91 | 47.39 | 10.13 | 0.8 |
| GM_A446718 | pMON97616 | 7.16 | 34.13 | 10.37 | 36.78 | 9.88 |
| GM_A433508 | pMON97617 | 6.73 | 34.03 | 10.3 | 45.31 | 1.33 |
| GM_A436385 | pMON97623 | 5.59 | 33.46 | 45.04 | 12.39 | 0.98 |
| GM_A436620 | pMON97623 | 5.03 | 32.64 | 47.41 | 11.59 | 0.88 |
| GM_A432534 | pMON97624 | 4.99 | 32.49 | 50.02 | 8.91 | 0.85 |
| GM_A432088 | pMON97624 | 4.37 | 32.29 | 50.51 | 9.51 | 0.95 |
| GM_A432084 | pMON97624 | 4.64 | 32.26 | 50.71 | 9.48 | 0.78 |
| GM_A446745 | pMON97616 | 5.44 | 31.25 | 48.12 | 11.82 | 1.04 |
| GM_A435561 | pMON97620 | 5.55 | 31.23 | 49.25 | 10.74 | 0.84 |
| GM_A446716 | pMON97616 | 5.44 | 31.12 | 43.54 | 16.31 | 1.37 |
| GM_A446708 | pMON97616 | 6.61 | 31.04 | 11.49 | 40.45 | 8.15 |
| GM_A432210 | pMON97624 | 5.45 | 30.75 | 48.69 | 11.48 | 1.15 |
| GM_A432525 | pMON97624 | 4.88 | 30.71 | 52.25 | 8.94 | 0.81 |
| GM_A432527 | pMON97624 | 4.23 | 30.22 | 55.18 | 7.09 | 0.72 |
| GM_A433487 | pMON97617 | 6.89 | 29.93 | 10.56 | 49.12 | 1.19 |
| GM_A435775 | pMON97620 | 5.46 | 29.6 | 51.98 | 9.27 | 1.04 |
| GM_A432344 | pMON97624 | 4.83 | 29.41 | 51.17 | 11.23 | 0.98 |
| GM_A436192 | pMON97623 | 6.59 | 29.36 | 16.94 | 37.47 | 7.44 |
| GM_A436184 | pMON97623 | 5.04 | 29.34 | 55.98 | 6.41 | 0.68 |
| GM_A435773 | pMON97620 | 5.49 | 29.24 | 50.88 | 11.19 | 0.85 |
| GM_A432080 | pMON97624 | 4.81 | 28.65 | 54.97 | 9.07 | 0.85 |
| GM_A432197 | pMON97624 | 5.72 | 28.13 | 45.77 | 17.11 | 1.21 |
| GM_A432337 | pMON97624 | 4.42 | 27.87 | 53.79 | 10.67 | 0.92 |
| GM_A432347 | pMON97624 | 4.57 | 27.86 | 52.83 | 11.36 | 1 |
| GM_A432512 | pMON97624 | 5.04 | 27.8 | 55.3 | 8.67 | 0.79 |
| GM_A432225 | pMON97624 | 5.29 | 27.49 | 51.47 | 12.12 | 1.2 |
| GM_A433184 | pMON97617 | 7.26 | 27.41 | 11.66 | 50.42 | 1.23 |
| GM_A432070 | pMON97624 | 5.04 | 27.27 | 50.56 | 13.85 | 0.93 |
| GM_A436392 | pMON97623 | 6.93 | 27.21 | 12.16 | 43.69 | 7.88 |
| GM_A432339 | pMON97624 | 5.23 | 26.73 | 52.2 | 12.4 | 1.02 |
| GM_A435541 | pMON97620 | 6.97 | 26.69 | 9.82 | 45.61 | 8.7 |
| GM_A432346 | pMON97624 | 4.56 | 26.67 | 53.85 | 11.42 | 0.98 |
| GM_A432537 | pMON97624 | 5.09 | 26.44 | 51.82 | 13.14 | 1.24 |
| GM_A432068 | pMON97624 | 6.63 | 26.42 | 13.08 | 44.08 | 7.86 |
| GM_A432513 | pMON97624 | 7.16 | 25.49 | 11.34 | 46.08 | 7.82 |
| GM_A436176 | pMON97623 | 5.33 | 24.95 | 56.31 | 10.24 | 0.88 |
| GM_A433502 | pMON97617 | 7.06 | 24.86 | 12.47 | 52.14 | 1.59 |
| GM_A433212 | pMON97617 | 6.99 | 24.64 | 12.08 | 52.89 | 1.31 |
| GM_A436628 | pMON97623 | 5.15 | 24.11 | 54.98 | 12.88 | 0.96 |
| GM_A432336 | pMON97624 | 4.85 | 24.07 | 57.37 | 10.53 | 0.92 |
| GM_A436195 | pMON97623 | 5.29 | 24 | 52.7 | 14.66 | 1.14 |
| GM_A432222 | pMON97624 | 4.99 | 23.6 | 56.8 | 11.52 | 0.85 |
| GM_A432340 | pMON97624 | 8.05 | 23.16 | 11.6 | 46.73 | 8.47 |
| GM_A432361 | pMON97624 | 5.01 | 22.75 | 57.97 | 10.74 | 1.16 |
| GM_A432354 | pMON97624 | 4.99 | 22.63 | 61.85 | 7.19 | 0.89 |
| GM_A432199 | pMON97624 | 4.8 | 22.61 | 57.3 | 12.84 | 0.86 |
| GM_A436605 | pMON97623 | 5.32 | 22.45 | 60.63 | 8.63 | 0.84 |
| GM_A433201 | pMON97617 | 7.88 | 22.27 | 15.21 | 51.78 | 0.99 |
| GM_A432220 | pMON97624 | 5.26 | 21.35 | 59.58 | 10.72 | 0.92 |
| GM_A433335 | pMON97617 | 7.67 | 21.04 | 14.61 | 53.53 | 1.3 |
| GM_A446712 | pMON97616 | 6.44 | 20.97 | 40.64 | 27.74 | 2.34 |
| GM_A436618 | pMON97623 | 5.68 | 18.9 | 61.04 | 11.47 | 0.95 |
| GM_A436178 | pMON97623 | 5.51 | 18.11 | 65.24 | 8.44 | 0.72 |
| GM_A432213 | pMON97624 | 8.62 | 17.54 | 13.5 | 49.55 | 8.98 |
| GM_A432076 | pMON97624 | 5.19 | 17.28 | 62.03 | 12.65 | 0.97 |
| GM_A432356 | pMON97624 | 6.03 | 17.19 | 58.93 | 14.51 | 1.33 |
| GM_A433499 | pMON97617 | 9.74 | 12.68 | 15.44 | 59.69 | 1.37 |
| GM_A432221 | pMON97624 | 10.1 | 12.64 | 14.32 | 51.13 | 10.35 |
| GM_A436382 | pMON97623 | 6.76 | 10.73 | 68.11 | 11.69 | 0.82 |
| GM_A446721 | pMON97616 | 6.89 | 8.89 | 68.72 | 12.66 | 1.15 |
| GM_A436014 | pMON97620 | 7.71 | 8.7 | 71.92 | 8.86 | 0.92 |
| GM_A432518 | pMON97624 | 7.15 | 8.6 | 68.2 | 13.32 | 1.11 |
| GM_A436003 | pMON97620 | 8.25 | 8.46 | 66.17 | 13.9 | 1.44 |
| GM_A436173 | pMON97623 | 8.53 | 8.21 | 57.36 | 22.87 | 1.47 |
| GM_A432200 | pMON97624 | 8.38 | 8.18 | 52.67 | 28.35 | 1.51 |
| GM_A446762 | pMON97616 | 8.53 | 7.98 | 63.08 | 17.51 | 1.44 |
| GM_A436193 | pMON97623 | 7.91 | 7.97 | 69.87 | 11.54 | 1.04 |
| GM_A432536 | pMON97624 | 8.9 | 7.84 | 56.31 | 23.57 | 1.48 |
| GM_A436612 | pMON97623 | 7.23 | 7.7 | 68.72 | 13.66 | 1.07 |
| GM_A433194 | pMON97617 | 12.25 | 7.05 | 12.29 | 65.47 | 1.51 |
| GM_A435537 | pMON97620 | 7.79 | 7.04 | 71.49 | 11 | 1.01 |
| GM_A433340 | pMON97617 | 13.03 | 6.96 | 11.33 | 65.95 | 1.84 |
| GM_A436175 | pMON97623 | 9.29 | 6.57 | 62.42 | 18.8 | 1.28 |
| GM_A435989 | pMON97620 | 12.88 | 6.29 | 17.54 | 56.77 | 5.33 |
| GM_A436002 | pMON97620 | 9.12 | 6.24 | 64.68 | 16.59 | 1.57 |
| GM_A433490 | pMON97617 | 11.98 | 6.19 | 16.82 | 56.01 | 8.24 |
| GM_A446736 | pMON97616 | 10.66 | 6.15 | 40.59 | 39.37 | 2.46 |
| GM_A432229 | pMON97624 | 8.63 | 6.08 | 66.3 | 16.2 | 1.36 |
| GM_A432529 | pMON97624 | 8.73 | 5.86 | 70.36 | 12.3 | 1.1 |
| GM_A432332 | pMON97624 | 8.18 | 5.27 | 69.22 | 14.4 | 1.38 |
| GM_A432077 | pMON97624 | 11.02 | 5.11 | 16.53 | 57.18 | 9.11 |
| GM_A433183 | pMON97617 | 11.38 | 5.08 | 14.27 | 59.3 | 9.29 |
| GM_A432227 | pMON97624 | 10.4 | 5.05 | 61.82 | 20.06 | 1.14 |
| GM_A433345 | pMON97617 | 12.63 | 4.79 | 16.89 | 56.22 | 8.89 |
| GM_A436590 | pMON97623 | 11.72 | 4.72 | 19.92 | 54.46 | 8.59 |
| GM_A446726 | pMON97616 | 9.73 | 4.67 | 59.1 | 22.9 | 2.38 |
| GM_A432223 | pMON97624 | 11.4 | 4.65 | 13.78 | 57.47 | 12.03 |
| GM_A432528 | pMON97624 | 11.23 | 4.63 | 18.3 | 56.29 | 8.54 |
| GM_A433208 | pMON97617 | 12.4 | 4.6 | 18.21 | 61.62 | 2.48 |
| GM_A436400 | pMON97623 | 12.75 | 4.56 | 15.33 | 56.34 | 10.02 |
| GM_A433494 | pMON97617 | 12.32 | 4.52 | 15.51 | 56.77 | 10.2 |
| GM_A435560 | pMON97620 | 11.71 | 4.46 | 13.96 | 57.41 | 11.98 |
| GM_A433196 | pMON97617 | 11.87 | 4.44 | 15.09 | 66.52 | 1.48 |
| GM_A432089 | pMON97624 | 11.24 | 4.39 | 15.4 | 59.57 | 8.86 |
| GM_A433199 | pMON97617 | 11.15 | 4.37 | 9.53 | 70.52 | 2.45 |
| GM_A436624 | pMON97623 | 9.76 | 4.33 | 26.92 | 53.57 | 4.83 |
| GM_A432351 | pMON97624 | 9.71 | 4.3 | 65.24 | 18.05 | 1.26 |
| GM_A446754 | pMON97616 | 11.81 | 4.27 | 18.95 | 56.16 | 8.3 |
| GM_A435536 | pMON97620 | 11.5 | 4.21 | 14.02 | 59.28 | 10.34 |
| GM_A432163 | pMON97624 | 13.41 | 4.17 | 16.73 | 56.05 | 9.36 |
| GM_A432514 | pMON97624 | 9.54 | 4.04 | 70.12 | 13.27 | 1.23 |
| GM_A432522 | pMON97624 | 9.66 | 3.99 | 70.75 | 13.21 | 1.08 |
| GM_A432509 | pMON97624 | 11.18 | 3.98 | 47.31 | 34.15 | 2.11 |
| GM_A432167 | pMON97624 | 11.35 | 3.98 | 15.98 | 58.41 | 9.35 |
| GM_A433205 | pMON97617 | 11.76 | 3.96 | 17.82 | 63.02 | 2.81 |
| GM_A433481 | pMON97617 | 11.77 | 3.95 | 18.39 | 59.98 | 5.52 |
| GM_A436170 | pMON97623 | 9.29 | 3.8 | 73.46 | 10.72 | 1.01 |
| GM_A436610 | pMON97623 | 9.7 | 3.8 | 68.81 | 15.67 | 1.32 |
| GM_A433206 | pMON97617 | 11.05 | 3.75 | 22.89 | 54.22 | 7.14 |
| GM_A433198 | pMON97617 | 13.21 | 3.75 | 15.74 | 64.8 | 1.45 |
| GM_A446711 | pMON97616 | 9.42 | 3.74 | 64.71 | 19.11 | 1.66 |
| GM_A435785 | pMON97620 | 12.69 | 3.7 | 22.62 | 55.94 | 4.05 |
| GM_A435778 | pMON97620 | 12.25 | 3.69 | 40.31 | 39.97 | 2.88 |
| GM_A433485 | pMON97617 | 12.2 | 3.64 | 17.94 | 61.69 | 3.52 |
| GM_A446753 | pMON97616 | 10.5 | 3.63 | 50.01 | 30.6 | 2.82 |
| GM_A433204 | pMON97617 | 12.63 | 3.62 | 14.13 | 66.87 | 1.83 |
| GM_A436169 | pMON97623 | 12.52 | 3.61 | 18.35 | 57.28 | 7.32 |
| GM_A446737 | pMON97616 | 10.45 | 3.6 | 28.8 | 51.36 | 4.72 |
| GM_A436398 | pMON97623 | 9.01 | 3.58 | 72.92 | 12.04 | 1.12 |
| GM_A433339 | pMON97617 | 13.01 | 3.51 | 16.17 | 63.19 | 3.09 |
| GM_A436404 | pMON97623 | 9.25 | 3.5 | 72.84 | 11.38 | 1.25 |
| GM_A436591 | pMON97623 | 10.06 | 3.47 | 65.18 | 18.67 | 1.6 |

TABLE 1-continued

Fatty Acid Composition of R1 Seeds

| Event | Construct | 16:0 | 18:0 | 18:1 | 18:2 | 18:3 |
|---|---|---|---|---|---|---|
| GM__A446758 | pMON97616 | 11.16 | 3.47 | 58.17 | 24.61 | 1.72 |
| GM__A435519 | pMON97620 | 9.52 | 3.3 | 72.42 | 11.48 | 1.32 |
| GM__A436011 | pMON97620 | 10.81 | 3.27 | 37.27 | 44.69 | 2.84 |
| GM__A435787 | pMON97620 | 10.68 | 3.24 | 54.52 | 28.24 | 2.15 |
| GM__A436595 | pMON97623 | 9.49 | 3.16 | 73.61 | 11.41 | 1.01 |
| GM__A436194 | pMON97623 | 9.86 | 3.05 | 71.84 | 12.61 | 1.22 |
| GM__A436383 | pMON97623 | 10.74 | 3.03 | 70.2 | 13.29 | 1.24 |
| GM__A436185 | pMON97623 | 9.8 | 3.03 | 70.02 | 14.21 | 1.47 |
| GM__A432166 | pMON97624 | 11.19 | 2.98 | 69.23 | 14.13 | 1.33 |
| GM__A436378 | pMON97623 | 9.24 | 2.89 | 74.79 | 10.38 | 1.18 |
| GM__A432516 | pMON97624 | 9.85 | 2.88 | 72.36 | 12.19 | 1.19 |
| GM__A436606 | pMON97623 | 10.29 | 2.87 | 56.06 | 27.8 | 2.17 |
| GM__A436015 | pMON97620 | 10.01 | 2.85 | 63.15 | 20.46 | 1.96 |
| GM__A436384 | pMON97623 | 9.69 | 2.77 | 66.75 | 17.71 | 1.34 |
| GM__A432350 | pMON97624 | 8.8 | 2.75 | 75.7 | 10.05 | 1.21 |
| GM__A433501 | pMON97617 | 10.13 | 2.74 | 43.4 | 38.62 | 4.15 |
| GM__A435999 | pMON97620 | 10.11 | 2.72 | 67.33 | 15.88 | 1.91 |

Suppression of the native FAD2 and FAD3 genes combined with the overexpression of the FATA gene from *Garcinia mangostana* gave seed oil with elevated stearate content, elevated oleic acid (OA) content, decreased linoleic acid (LA) content and decreased alpha linolenic acid (ALA) content. Using >6% as a measure for elevated stearate (HS), <5% as measure for lowered ALA (LL) and a variable measure of elevated oleic content (MO) as it is dependent on the stearate level, we generated Table 2 which lists the numbers of events that fall into the various combinations of the three targeted fatty acid alterations of high stearate/increased oleic acid/low ALA. Seventeen events did not have an altered fatty acid profile and were classified as nulls. We observed stearate ranging from 2.72% up to 47.56%, OA from 5.85% up to 75.70% and ALA from 11.98% down to 0.68%. We have also observed the combination of all three modifications as well as intermediate combinations in single soy seed.

TABLE 2

Phenotype groups

| Phenotype | Event Number |
|---|---|
| HS/LL | 14 |
| HS/MO/LL | 72 |
| HS | 8 |
| LL | 10 |
| MO/LL | 34 |
| Null | 17 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

All publications and patent applications cited in this specification are herein incorporated by reference as if each individual publication or patent application was specifically and individually indicated to be incorporated by reference.

What is claimed is:

1. A soybean seed comprising an oleic acid content of 35% to 57% by weight of total seed fatty acids, a stearic acid content of at least 35% by weight of total seed fatty acids, and a linolenic acid content of 0.68% to 1.14% by weight of total seed fatty acids.

2. The soybean seed of claim 1 wherein the stearic acid content is 35% to 45.5% by weight of total seed fatty acids.

3. The soybean seed of claim 1 wherein the stearic acid content is 35% to 45.5% by weight of total seed fatty acids and the oleic acid content is 39% to 57% by weight of total seed fatty acids.

4. The soybean seed of claim 1 wherein the oleic acid content is 39 to 57% by weight of total seed fatty acids.

5. A soybean plant having seed comprising an oleic acid content of 35% to 57% by weight of total seed fatty acids, a stearic acid content of at least 35% by weight of total seed fatty acids, and a linolenic acid content of 0.68% to 1.14% by weight of total seed fatty acids, wherein said soybean plant is mature.

6. The soybean plant of claim 5, wherein the seed comprises a stearic acid content of 35% to 45.5% by weight of total seed fatty acids.

7. The soybean plant of claim 5 wherein the seed comprises a stearic acid content of 35% to 45.5% by weight of total seed fatty acids and an oleic acid content of 39% to 57% by weight of total seed fatty acids.

8. The soybean plant of claim 5 comprising in its genome a DNA construct comprising a DNA segment expressing a thioesterase with activity on stearoyl acyl ACP.

9. The soybean plant of claim 8 wherein the thioesterase is encoded by a FATA gene.

10. The soybean plant of claim 8 wherein the thioesterase is encoded by a mangosteen thioesterase gene.

11. The soybean plant of claim 5 further comprising a first DNA segment expressing a thioesterase with activity on stearoyl acyl ACP and a second DNA segment designed to trigger the suppression of endogenous FAD3 genes.

12. The soybean plant of claim 8 further comprising a first DNA segment expressing a thioesterase with activity on stearoyl acyl ACP and a second DNA segment designed to trigger the suppression of endogenous FAD2 and FAD3 genes.

13. The soybean seed of claim 1, wherein the seed is transgenic and comprises a DNA construct comprising a DNA segment expressing a thioesterase with activity on stearoyl acyl ACP.

14. The soybean seed of claim 13 wherein the thioesterase is encoded by a FATA gene.

15. The soybean seed of claim 13 wherein the thioesterase is encoded by a mangosteen thioesterase gene.

16. The soybean seed of claim 13 further comprising a first DNA segment expressing a thioesterase with activity on stearoyl acyl ACP and a second DNA segment designed to trigger the suppression of an endogenous FAD3 gene.

17. The soybean seed of claim 13 further comprising a first DNA segment expressing a thioesterase with activity on stearoyl acyl ACP and a second DNA segment designed to trigger the suppression of endogenous FAD2 and FAD3 genes.

18. A method for producing a soybean seed crop, the seed of said crop having an oil composition comprising an oleic acid content of 35% to 57% by weight of total seed fatty acids, a stearic acid content of at least 35% by weight of total seed fatty acids, and a linolenic acid content of 0.68% to 1.14% by weight of total seed fatty acids upon heptane extraction, comprising growing the soybean plant of claim 5 to maturity under plant growth conditions; and harvesting seeds from said plant to form the soybean seed crop.

19. The method of claim 18, wherein the soybean plant comprises in its genome a DNA construct comprising a DNA segment expressing a thioesterase with activity on stearoyl acyl ACP.

20. The method of claim 18, wherein the soybean plant comprises in its genome a first DNA segment expressing a thioesterase with activity on stearoyl acyl ACP and a second DNA segment designed to trigger the suppression of endogenous FAD2 and FAD3 genes.

* * * * *

SEQUENCE LISTING

```
<160> NUMBER OF SEQ ID NOS: 7

<210> SEQ ID NO 1
<211> LENGTH: 352
<212> TYPE: PRT
<213> ORGANISM: Garcinia mangostana

<400> SEQUENCE: 1

Met Leu Lys Leu Ser Ser Ser Arg Ser Pro Leu Ala Arg Ile Pro Thr
1               5                   10                  15

Arg Pro Arg Pro Asn Ser Ile Pro Pro Arg Ile Ile Val Val Ser Ser
            20                  25                  30

Ser Ser Ser Lys Val Asn Pro Leu Lys Thr Glu Ala Val Val Ser Ser
        35                  40                  45

Gly Leu Ala Asp Arg Leu Arg Leu Gly Ser Leu Thr Glu Asp Gly Leu
    50                  55                  60

Ser Tyr Lys Glu Lys Phe Ile Val Arg Cys Tyr Glu Val Gly Ile Asn
65                  70                  75                  80

Lys Thr Ala Thr Val Glu Thr Ile Ala Asn Leu Leu Gln Glu Val Gly
                85                  90                  95

Cys Asn His Ala Gln Ser Val Gly Tyr Ser Thr Gly Gly Phe Ser Thr
            100                 105                 110

Thr Pro Thr Met Arg Lys Leu Arg Leu Ile Trp Val Thr Ala Arg Met
        115                 120                 125
```

```
His Ile Glu Ile Tyr Lys Tyr Pro Ala Trp Ser Asp Val Val Glu Ile
        130                 135                 140

Glu Ser Trp Gly Gln Gly Glu Gly Lys Ile Gly Thr Arg Arg Asp Trp
145                 150                 155                 160

Ile Leu Arg Asp Tyr Ala Thr Gly Gln Val Ile Gly Arg Ala Thr Ser
                165                 170                 175

Lys Trp Val Met Met Asn Gln Asp Thr Arg Arg Leu Gln Lys Val Asp
                180                 185                 190

Val Asp Val Arg Asp Glu Tyr Leu Val His Cys Pro Arg Glu Leu Arg
            195                 200                 205

Leu Ala Phe Pro Glu Gly Asn Asn Ser Ser Leu Lys Lys Ile Ser Lys
210                 215                 220

Leu Glu Asp Pro Ser Gln Tyr Ser Lys Leu Gly Leu Val Pro Arg Arg
225                 230                 235                 240

Ala Asp Leu Asp Met Asn Gln His Val Asn Asn Val Thr Tyr Ile Gly
                245                 250                 255

Trp Val Leu Glu Ser Met Pro Gln Glu Ile Ile Asp Thr His Glu Leu
                260                 265                 270

Gln Thr Ile Thr Leu Asp Tyr Arg Arg Glu Cys Gln His Asp Asp Val
            275                 280                 285

Val Asp Ser Leu Thr Ser Pro Glu Pro Ser Glu Asp Ala Glu Ala Val
290                 295                 300

Phe Asn His Asn Gly Thr Asn Gly Ser Ala Asn Val Ser Ala Asn Asp
305                 310                 315                 320

His Gly Cys Arg Asn Phe Leu His Leu Leu Arg Leu Ser Gly Asn Gly
                325                 330                 335

Leu Glu Ile Asn Arg Gly Arg Thr Glu Trp Arg Lys Lys Pro Thr Arg
            340                 345                 350

<210> SEQ ID NO 2
<211> LENGTH: 1059
<212> TYPE: DNA
<213> ORGANISM: Garcinia mangostana

<400> SEQUENCE: 2
atgttgaagc tctcttcttc ccgaagccca ttggcccgca ttccacccg gcccaggccc     60 aactccattc ctccccggat aattgtggtt tcctcctcat ccagcaaggt taatccactc    120
aaaacagagg cggtggtttc ttcggggctg gctgaccggc tccggctggg cagcttgacc    180
gaggacgggc tttcgtataa ggagaagttc atagtgagat gctatgaggt tgggattaac    240
aagaccgcta ctgttgagac tattgccaac ctcttgcagg aggttggatg caatcacgcc    300
caaagcgttg atattcgac gggtgggttt tcgacaaccc ctaccatgag aaaattgcgt     360
ctgatatggg ttactgctcg catgcacatc gaaatctaca atatccagc ttggagtgat    420 gtggtggaaa tagagtcgtg gggccagggt gaaggaaaaa tcggaaccag acgtgattgg    480
attctgagag actatgccac tggtcaagtt attggccgag ctactagcaa gtgggtaatg    540
atgaaccaag acaccaggcg acttcaaaaa gtcgatgttg atgttcgtga tgagtacttg    600
gttcactgtc caagagaact cagattggca tttccagagg aaaataatag cagcttgaag    660
aaaatttcaa aacttgaaga tccttctcaa tattcgaagc tggggcttgt gcctagaaga    720
gcagatctgg acatgaatca acatgttaat aatgtcacct atattggatg ggtgttggag    780
agcatgcctc aagaaatcat tgatacccat gaactgcaaa ccataacatt agactacaga    840
cgggaatgcc aacatgatga tgtggttgat ccttgactag tccagagcc ttctgaagat    900
```

| | | |
|---|---|---|
| gctgaagcag ttttcaacca taatggaaca aatgggtctg caaatgtgag cgccaacgac | 960 | |
| catgatgcc gcaactttct gcatctacta agattgtcgg gcaatggact tgaaatcaac | 1020 | |
| cgtggtcgta ctgagtggag aaagaaacct acaagatga | 1059 | |

<210> SEQ ID NO 3
<211> LENGTH: 5387
<212> TYPE: DNA
<213> ORGANISM: Artificial
<220> FEATURE:
<223> OTHER INFORMATION: Cassette

<400> SEQUENCE: 3

| | |
|---|---|
| aggattttc ggcgctgcgc tacgtccgcg accgcgttga gggatcaagc cacagcagcc | 60 |
| cactcgacct tctagccgac ccagacgagc caagggatct ttttggaatg ctgctccgtc | 120 |
| gtcaggcttt ccgacgtttg ggtggttgaa cagaagtcat tatcgcacgg aatgccaagc | 180 |
| actcccgagg ggaaccctgt ggttggcatg cacatacaaa tggacgaacg gataaacctt | 240 |
| ttcacgccct tttaaatatc cgattattct aataaacgct cttttctctt aggtttaccc | 300 |
| gccaatatat cctgtcaaac actgatagtt taaactgaag gcgggaaacg acaatctgat | 360 |
| ccccatcaag ctagcttctg caggtcctgc tcgagcggcc gctctagaac tagtggatcc | 420 |
| aactcaaccc atcatgagcc acacatttg ttgtttctaa cccaacctca aactcgtatt | 480 |
| ctcttccgcc acctcatttt tgtttatttc aacacccgtc aaactgcatg ccaccccgtg | 540 |
| gccaaatgtc catgcatgtt aacaagacct atgactataa atatctgcaa tctcggccca | 600 |
| ggtttcatc atcaagaacc cctaggccaa gatgttgaag ctctcttctt cccgaagccc | 660 |
| attggcccgc attcccaccc ggcccaggcc caactccatt cctccccgga taattgtggt | 720 |
| ttcctcctca tccagcaagg ttaatccact caaaacagag gcggtggttt cttcggggct | 780 |
| ggctgaccgg ctccggctgg gcagcttgac cgaggacggg cttcgtata aggagaagtt | 840 |
| catagtgaga tgctatgagg ttgggattaa caagaccgct actgttgaga ctattgccaa | 900 |
| cctcttgcag gaggttggat gcaatcacgc ccaaagcgtt ggatattcga cgggtgggtt | 960 |
| ttcgacaacc cctaccatga gaaaattgcg tctgatatgg ttactgctc gcatgcacat | 1020 |
| cgaaatctac aaatatccag cttggagtga tgtggtggaa atagagtcgt ggggccaggg | 1080 |
| tgaaggaaaa atcggaacca gacgtgattg gattctgaga gactatgcca ctggtcaagt | 1140 |
| tattggccga gctactagca agtgggtaat gatgaaccaa gacaccaggc gacttcaaaa | 1200 |
| agtcgatgtt gatgttcgtg atgagtactt ggttcactgt ccaagagaac tcagattggc | 1260 |
| atttccagag gaaaataata gcagcttgaa gaaaatttca aaacttgaag atccttctca | 1320 |
| atattcgaag ctggggcttg tgcctagaag agcagatctg gacatgaatc aacatgttaa | 1380 |
| taatgtcacc tatattggat gggtgttgga gagcatgcct caagaaatca ttgatccca | 1440 |
| tgaactgcaa accataacat tagactacag acgggaatgc caacatgatg atgtggttga | 1500 |
| ttccttgact agtccagagc cttctgaaga tgctgaagca gttttcaacc ataatggaac | 1560 |
| aaatgggtct gcaaatgtga gcgccaacga ccatggatgc cgcaactttc tgcatctact | 1620 |
| aagattgtcg gcaatggac ttgaaatcaa ccgtggtcgt actgagtgga gaaagaaacc | 1680 |
| tacaagatga ctcgagagtg tgtataccac ggtgatatga gtgtggttgt tgatgtatgt | 1740 |
| taacactaca tagtcatggt gtgtgttcca taaataatgt actaatgtaa taagaactac | 1800 |
| tccgtagacg gtaataaaag agaagttttt ttttttactc ttgctacttt cctataaagt | 1860 |

```
gatgattaac aacagataca ccaaaaagaa acaattaat ctatattcac aatgaagcag     1920
tactagtcta ttgaacatgt cagattttct ttttctaaat gtctaattaa gccttcaagg     1980
ctagtgatga taaaagatca tccaatgggc ggccgcgggt ccggcggccg cggtacggtc     2040
gactctagag gatccccggc aaaaacattt aatacgtatt atttaagaaa aaatatgta     2100 ataatatatt tatattttaa tatctattct tatgtatttt ttaaaaatct attatatatt     2160
gatcaactaa aatattttta tatctacact tattttgcat ttttatcaat tttcttgcgt     2220
tttttggcat atttaataat gactattctt taataatcaa tcattattct tacatggtac     2280
atattgttgg aaccatatga agtgtccatt gcatttgact atgtggatag tgttttgatc     2340
caggcctcca tttgccgctt attaattaat ttggtaacag tccgtactaa tcagttactt     2400
atccttcctc catcataatt aatcttggta gtctcgaatg ccacaacact gactagtctc     2460
ttggatcata agaaaaagcc aaggaacaaa agaagacaaa acacaatgag agtatccttt     2520
gcatagcaat gtctaagttc ataaaattca acaaaaacg caatcacaca cagtggacat     2580
cacttatcca ctagctgatc aggatcgccg cgtcaagaaa aaaaaactgg accccaaaag     2640
ccatgcacaa caacacgtac tcacaaaggt gtcaatcgag cagcccaaaa cattcaccaa     2700
ctcaacccat catgagccca cacatttgtt gtttctaacc caacctcaaa ctcgtattct     2760
cttccgccac ctcattttg tttatttcaa cacccgtcaa actgcatgcc acccgtggc     2820 caaatgtcca tgcatgttaa caagacctat gactataaat atctgcaatc tcggcccagg     2880
ttttcatcat caagaaccgg gtaccgagct cgagcgtacg cctaggctcg aggtaaatta     2940
aattgtgcct gcacctcggg atatttcatg tggggttcat catatttgtt gaggaaaaga     3000
aactcccgaa attgaattat gcatttatat atccttttc atttctagat ttcctgaagg     3060
cttaggtgta ggcacctagc tagtagctac aatatcagca cttctctcta ttgataaaca     3120
attggctgta atgccgcagt agaggacgat cagtaacaga gaaagaaaca tttgagcaag     3180
tttttgatgc tacattttacc tatttcactc ttaaatacta tttcctatgt aatatgtaat     3240
ttagaatatg ttacctactc aaatcaatta ggtgacatgt ataagctttc ataaattatg     3300
ctagaaatgc acttactttt caaagcatgc tatgtcaaaa gatttcattc ttcctcttct     3360
aggttattac gcaccaccca ccacgtatcc ctgaaaagag agaaaaacac actaagccaa     3420
agccaaagca gcaagttatt tattggattc tagctactca aattactttt tttttaatgt     3480 tacgttttg gagttttaac gttttctgaa caacttgcaa attacatgca tagagagaca     3540
ggaattcata gtgggcctca atggaatatt tatttgaaat tagtaaggtg gtaactagtc     3600
tagagagctc accggtggtt taggaattaa aggaacggtg ggctggtaat gaacgccatt     3660
gattcttcga acgcatgcgc taatgttaga aggcccgcta gtaggaacgc acttctcccg     3720
ggtgcggccg catttaaata ctagttacca ccttactaat ttcaaataaa tattccattg     3780
aggcccacta tgaattcctg tctctctatg catgtaattt gcaagttgtt cagaaaacgt     3840
taaaactcca aaaacgtaac attaaaaaaa aagtaatttg agtagctaga atccaataaa     3900
taacttgctg ctttggcttt ggcttagtgt gttttttctct cttttcaggg atacgtggtg     3960
ggtggtgcgt aataacctag aagaggaaga atgaaatctt ttgacatagc atgctttgaa     4020
aagtaagtgc atttctagca taatttatga aagcttatac atgtcaccta attgatttga     4080
gtaggtaaca tattctaaat tacatattac ataggaaata gtatttaaga gtgaaatagg     4140
taaatgtagc atcaaaaact tgctcaaatg tttcttctc tgttactgat cgtcctctac     4200
tgcggcatta cagccaattg tttatcaata gagagaagtg ctgatattgt agctactagc     4260
```

```
taggtgccta cacctaagcc ttcaggaaat ctagaaatga aaaggatat ataaatgcat    4320
aattcaattt cgggagtttc ttttcctcaa caaatatgat gaaccccaca tgaaatatcc    4380
cgaggtgcag gcacaattta atttacctcg agcctaggcg tacagcccgg ctccaaggcc    4440
gtggggtacg aacaaaagag tgcctcacat ttgatgcaat agctctgtaa tgtttcattc    4500
atttgcttat ttcggccttg ttttctcgt attctatggg ctgatgtctc atatgggact    4560
tttctactag agagcctacg ttactttacc attatattgt attctttgag acattattat    4620
tatttttta ccttttgagg acactctttt tttgtatttg aaggaattta ttgtttattt    4680
tgtttggaat atgtttggtt ggattattc gattcatata tattatataa agtaattat    4740
gttattaaga aacgtagtaa gaacttacaa atataaggat cgaatcccga acttcatgca    4800
aatcaattta caacccacac aagtttaaca ttaaattaac gtgattggtt agtaaattca    4860
tgtttctctg tttaatttgt tgaattgggt cccatatata tatagcgatc gcatatatat    4920
ataggcgcgc caaatcgtga agtttctcat ctaagccccc atttggacgt gaatgtagac    4980
acgtcgaaat aaagatttcc gaattagaat aatttgttta ttgctttcgc ctataaatac    5040
gacggatcgt aatttgtcgt tttatcaaaa tgtactttca ttttataata acgctgcgga    5100
catctacatt tttgaattga aaaaaattg gtaattactc tttcttttc tccatattga    5160
ccatcatact cattgctgat ccatgtagat ttcccggaca tgaagccatt tacaattgaa    5220
tatatcctgc cgccgctgcc gctttgcacc cggtggagct tgcatgttgg tttctacgca    5280
gaactgagcc ggttaggcag ataatttcca ttgagaactg agccatgtgc accttccccc    5340
caacacggtg agcgacgggg caacggagtg atccacatgg gactttt                 5387
```

<210> SEQ ID NO 4
<211> LENGTH: 4945
<212> TYPE: DNA
<213> ORGANISM: Artificial
<220> FEATURE:
<223> OTHER INFORMATION: Cassette

<400> SEQUENCE: 4

```
aggattttc ggcgctgcgc tacgtccgcg accgcgttga gggatcaagc cacagcagcc      60
cactcgacct tctagccgac ccagacgagc caagggatct ttttggaatg ctgctccgtc     120
gtcaggcttt ccgacgtttg ggtggttgaa cagaagtcat tatcgcacgg aatgccaagc     180
actcccgagg ggaaccctgt ggttggcatg cacatacaaa tggacgaacg gataaacctt     240
ttcacgcct tttaaatatc cgattattct aataaacgct cttttctctt aggtttaccc     300
gccaatatat cctgtcaaac actgatagtt taaactgaag gcgggaaacg acaatctgat     360
ccccatcaag ctagcttctg caggtcctgc tcgagcggcc gctctagaac tagtggatcc     420
aactcaaccc atcatgagcc cacacatttg ttgtttctaa cccaacctca aactcgtatt     480
ctcttccgcc acctcatttt tgtttatttc aacacccgtc aaactgcatg ccaccccgtg     540
gccaaatgtc catgcatgtt aacaagacct atgactataa atatctgcaa tctcggccca     600
ggttttcatc atcaagaacc cctaggccaa gatgttgaag ctctcttctt cccgaagccc     660
attggcccgc attcccaccc ggcccaggcc caactccatt cctccccgga taattgtggt     720
ttcctcctca tccagcaagg ttaatccact caaaacagag gcggtggttt cttcggggct     780
ggctgaccgg ctccgctgg gcagcttgac cgaggacggg cttcgtata aggagaagtt     840
catagtgaga tgctatgagg ttgggattaa caagaccgct actgttgaga ctattgccaa     900
```

```
cctcttgcag gaggttggat gcaatcacgc ccaaagcgtt ggatattcga cgggtgggtt      960
ttcgacaacc cctaccatga gaaaattgcg tctgatatgg ttactgctc gcatgcacat     1020 cgaaatctac aaatatccag cttggagtga tgtggtggaa atagagtcgt ggggccaggg    1080
tgaaggaaaa atcggaacca gacgtgattg gattctgaga gactatgcca ctggtcaagt    1140
tattggccga gctactagca agtgggtaat gatgaaccaa gacaccaggc gacttcaaaa    1200
agtcgatgtt gatgttcgtg atgagtactt ggttcactgt ccaagagaac tcagattggc    1260
atttccagag gaaaataata gcagcttgaa gaaaatttca aaacttgaag atccttctca    1320
atattcgaag ctggggcttg tgcctagaag agcagatctg gacatgaatc aacatgttaa    1380
taatgtcacc tatattggat gggtgttgga gagcatgcct caagaaatca ttgatacccca   1440 tgaactgcaa accataacat agactacag acgggaatgc caacatgatg atgtggttga    1500
ttccttgact agtccagagc cttctgaaga tgctgaagca gttttcaacc ataatggaac    1560
aaatgggtct gcaaatgtga cgccaacga ccatggatgc cgcaactttc tgcatctact    1620
aagattgtcg ggcaatggac ttgaaatcaa ccgtggtcgt actgagtgga gaaagaaacc    1680
tacaagatga ctcgagagtg tgtataccac ggtgatatga gtgtggttgt tgatgtatgt    1740
taacactaca tagtcatggt gtgtgttcca taaataatgt actaatgtaa taagaactac    1800
tccgtagacg gtaataaaag agaagttttt ttttttactc ttgctacttt cctataaagt    1860
gatgattaac aacagataca ccaaaaagaa aacaattaat ctatattcac aatgaagcag    1920
tactagtcta ttgaacatgt cagattttct ttttctaaat gtctaattaa gccttcaagg    1980
ctagtgatga taaaagatca tccaatgggc ggccgcgggt ccggcggccg cggtacggtc    2040
gactctagag gatccccggc aaaaacattt aatacgtatt atttaagaaa aaaatatgta    2100
ataatatatt tatatttaa tatctattct tatgtatttt ttaaaaatct attatatatt    2160
gatcaactaa aatattttta tatctacact tattttgcat ttttatcaat tttcttgcgt    2220
tttttggcat atttaataat gactattctt taataatcaa tcattattct tacatggtac    2280
atattgttgg aaccatatga agtgtccatt gcatttgact atgtggatag tgttttgatc    2340
caggcctcca tttgccgctt attaattaat ttggtaacag tccgtactaa tcagttactt    2400
atccttcctc catcataatt aatcttggta gtctcgaatg ccacaacact gactagtctc    2460
ttggatcata agaaaaagcc aaggaacaaa agaagacaaa acacaatgag agtatccttt    2520
gcatagcaat gtctaagttc ataaaattca acaaaaacg caatcacaca cagtggacat    2580
cacttatcca ctagctgatc aggatcgccg cgtcaagaaa aaaaactgg accccaaaag    2640 ccatgcacaa caacacgtac tcacaaaggt gtcaatcgag cagcccaaaa cattcaccaa    2700
ctcaacccat catgagccca cacatttgtt gtttctaacc caacctcaaa ctcgtattct    2760
cttccgccac ctcatttttg tttatttcaa cacccgtcaa actgcatgcc acccgtggc    2820 caaatgtcca tgcatgttaa caagacctat gactataaat atctgcaatc tcggcccagg    2880
ttttcatcat caagaaccgg gtaccgagct cgagcgtacg cctaggctcg agtaacagag    2940
aaagaaacat ttgagcaagt ttttgatgct acatttacct atttcactct taaatactat    3000
ttcctatgta atatgtaatt tagaaatatgt tacctactca aatcaattag gtgacatgta    3060
taagctttca taaattatgc tagaaatgca cttactttc aaagcatgct atgtcaaaag    3120
atttcattct tcctcttcta ggttattacg caccacccac cacgtatccc tgaaaagaga    3180
gaaaaacaca ctaagccaaa gccaaagcag caagttattt attggattct agctactcaa    3240
attacttttt ttttaatgtt acgttttttgg agttttaacg ttttctgaac aacttgcaaa    3300
```

```
ttacatgcat agagagacag gaattcatag tgggcctcaa tggaatattt atttgaaatt    3360
agtaaggtgg taactagtct agagagctca ccggtggttt aggaattaaa ggaacggtgg    3420
gctggtaatg aacgccattg attcttcgaa cgcatgcgct aatgttagaa ggcccgctag    3480
taggaacgca cttctcccgg gtgcggccgc atttaaatac tagttaccac cttactaatt    3540
tcaaataaat attccattga ggcccactat gaattcctgt ctctctatgc atgtaatttg    3600
caagttgttc agaaaacgtt aaaactccaa aaacgtaaca ttaaaaaaaa agtaatttga    3660
gtagctagaa tccaataaat aacttgctgc tttggctttg cttagtgtg tttttctctc     3720 ttttcaggga tacgtggtgg gtggtgcgta ataacctaga agaggaagaa tgaaatcttt    3780
tgacatagca tgctttgaaa agtaagtgca tttctagcat aatttatgaa agcttataca    3840
tgtcacctaa ttgatttgag taggtaacat attctaaatt acatattaca taggaaatag    3900
tatttaagag tgaaataggt aaatgtagca tcaaaaactt gctcaaatgt ttctttctct    3960
gttactcgag cctaggcgta cagcccggct ccaaggccgt ggggtacgaa caaaagagtg    4020
cctcacattt gatgcaatag ctctgtaatg tttcattcat ttgcttattt cggccttgtt    4080
tttctcgtat tctatgggct gatgtctcat atgggacttt tctactagag agcctacgtt    4140
actttaccat tatattgtat tctttgagac attattatta tttttttacc ttttgaggac    4200
actctttttt tgtatttgaa ggaatttatt gtttattttg tttggaatat gtttggttgg    4260
atttattcga ttcatatata ttatataaaa gtaattatgt tattaagaaa cgtagtaaga    4320
acttacaaat ataaggatcg aatcccgaac ttcatgcaaa tcaatttaca acccacacaa    4380
gtttaacatt aaattaacgt gattggttag taaattcatg tttctctgtt taatttgttg    4440
aattgggtcc catatatata tagcgatcgc atatatatat aggcgcgcca atcgtgaag    4500 tttctcatct aagcccccat ttggacgtga atgtagacac gtcgaaataa agatttccga    4560
attagaataa tttgtttatt gctttcgcct ataaatacga cggatcgtaa tttgtcgttt    4620
tatcaaaatg tactttcatt ttataataac gctgcggaca tctacatttt tgaattgaaa    4680
aaaaattggt aattactctt tcttttctc catattgacc atcatactca ttgctgatcc     4740
atgtagattt cccggacatg aagccattta caattgaata tatcctgccg ccgctgccgc    4800
tttgcacccg gtggagcttg catgttggtt tctacgcaga actgagccgg ttaggcagat    4860
aatttccatt gagaactgag ccatgtgcac cttcccccca acacggtgag cgacggggca    4920
acggagtgat ccacatggga ctttt                                         4945
```

<210> SEQ ID NO 5
<211> LENGTH: 6151
<212> TYPE: DNA
<213> ORGANISM: Artificial
<220> FEATURE:
<223> OTHER INFORMATION: Cassette

<400> SEQUENCE: 5

```
aggattttc ggcgctgcgc tacgtccgcg accgcgttga gggatcaagc cacagcagcc       60
cactcgacct tctagccgac ccagacgagc caagggatct ttttggaatg ctgctccgtc     120
gtcaggcttt ccgacgtttg ggtggttgaa cagaagtcat tatcgcacgg aatgccaagc    180
actcccgagg ggaaccctgt ggttggcatg cacatacaaa tggacgaacg gataaacctt    240
ttcacgccct tttaaatatc cgattattct aataaacgct ctttctctt aggtttaccc     300 gccaatatat cctgtcaaac actgatagtt taaactgaag gcgggaaacg acaatctgat    360
```

-continued

```
ccccatcaag ctagcttctg caggtcctgc tcgagcggcc gctctagaac tagtggatcc      420
aactcaaccc atcatgagcc acacatttg ttgtttctaa cccaacctca aactcgtatt       480
ctcttccgcc acctcatttt tgtttatttc aacacccgtc aaactgcatg ccaccccgtg     540
gccaaatgtc catgcatgtt aacaagacct atgactataa atatctgcaa tctcggccca     600
ggttttcatc atcaagaacc cctaggccaa gatgttgaag ctctcttctt cccgaagccc     660
attggcccgc attccaccc ggcccaggcc caactccatt cctccccgga taattgtggt      720
ttcctcctca tccagcaagg ttaatccact caaaacagag gcggtggttt cttcggggct     780
ggctgaccgg ctccggctgg gcagcttgac cgaggacggg ctttcgtata aggagaagtt     840
catagtgaga tgctatgagg ttgggattaa caagaccgct actgttgaga ctattgccaa     900
cctcttgcag gaggttggat gcaatcacgc ccaaagcgtt ggatattcga cgggtgggtt     960
ttcgacaacc cctaccatga gaaaattgcg tctgatatgg ttactgctc gcatgcacat     1020 cgaaatctac aaatatccag cttggagtga tgtggtggaa atagagtcgt ggggccaggg    1080
tgaaggaaaa atcggaacca gacgtgattg gattctgaga gactatgcca ctggtcaagt    1140
tattggccga gctactagca agtgggtaat gatgaaccaa gacaccaggc gacttcaaaa    1200
agtcgatgtt gatgttcgtg atgagtactt ggttcactgt ccaagagaac tcagattggc    1260
atttccagag gaaaataata gcagcttgaa gaaaatttca aaacttgaag atccttctca    1320
atattcgaag ctggggcttg tgcctagaag agcagatctg gacatgaatc aacatgttaa    1380
taatgtcacc tatattggat gggtgttgga gagcatgcct caagaaatca ttgatccca    1440 tgaactgcaa accataacat agactacag acgggaatgc caacatgatg atgtggttga    1500
ttccttgact agtccagagc cttctgaaga tgctgaagca gttttcaacc ataatggaac    1560
aaatgggtct gcaaatgtga gcgccaacga ccatggatgc cgcaactttc tgcatctact    1620
aagattgtcg ggcaatggac ttgaaatcaa ccgtggtcgt actgagtgga gaaagaaacc    1680
tacaagatga ctcgagagtg tgtataccac ggtgatatga gtgtggttgt tgatgtatgt    1740
taacactaca tagtcatggt gtgtgttcca taaataatgt actaatgtaa taagaactac    1800
tccgtagacg gtaataaaag agaagttttt tttttactc ttgctacttt cctataaagt     1860
gatgattaac aacagataca ccaaaaagaa acaattaat ctatattcac aatgaagcag      1920
tactagtcta ttgaacatgt cagattttct ttttctaaat gtctaattaa gccttcaagg    1980
ctagtgatga taaagatca tccaatgggc ggccgcgggt ccggcggccg cggtacggtc     2040
gactctagag gatccccggc aaaaacattt aatacgtatt atttaagaaa aaatatgta     2100 ataatatatt tatattttaa tatctattct tatgtatttt ttaaaaatct attatatatt    2160
gatcaactaa aatatttta tatctacact tattttgcat ttttatcaat tttcttgcgt     2220
tttttggcat atttaataat gactattctt taataatcaa tcattattct tacatggtac    2280
atattgttgg aaccatatga agtgtccatt gcatttgact atgtggatag tgttttgatc    2340
caggcctcca tttgccgctt attaattaat ttggtaacag tccgtactaa tcagttactt    2400
atccttcctc catcataatt aatcttggta gtctcgaatg ccacaacact gactagtctc    2460
ttggatcata agaaaagcc aaggaacaaa agaagacaaa acacaatgag agtatccttt     2520
gcatagcaat gtctaagttc ataaaattca aacaaaaacg caatcacaca cagtggacat    2580
cacttatcca ctagctgatc aggatcgccg cgtcaagaaa aaaaactgg accccaaaag     2640 ccatgcacaa caacacgtac tcacaaaggt gtcaatcgag cagcccaaaa cattcaccaa    2700
ctcaacccat catgagccca cacatttgtt gtttctaacc caacctcaaa ctcgtattct    2760
```

```
cttccgccac ctcattttg tttatttcaa cacccgtcaa actgcatgcc acccgtggc      2820 caaatgtcca tgcatgttaa caagacctat gactataaat atctgcaatc tcggcccagg     2880
ttttcatcat caagaaccgg gtaccgagct cgagcgtacg cctaggctcg aggtaaatta     2940
aattgtgcct gcacctcggg atatttcatg tggggttcat catatttgtt gaggaaaaga    3000
aactcccgaa attgaattat gcatttatat atccttttc atttctagat ttcctgaagg     3060
cttaggtgta ggcacctagc tagtagctac aatatcagca cttctctcta ttgataaaca    3120
attggctgta atgccgcagt agaggacgat cacaacattt cgtgctggtt acttttgtt    3180 ttatggtcat gatttcactc tctctaatct ctccattcat tttgtagttg tcattatctt    3240 tagattttc acgatttcct tcttcctatt ctaggttttt acgcaccacg tatccctgag     3300
aaaagagagg aaccacactc tctaagccaa agcaaaagca gcagcagcag cagtttcaaa    3360 cttttttgggt tattatttat tggattctag ctactcaaat tactttttt ttaatgttat    3420 gttttttgga gttaacgtt ttctgaacaa cttgcaaatt acttgcatag agagacatgg     3480
aatatttatt tgaaattagt aaggtagtaa taataaattt tgaattgtca gtttgtaaca    3540
gagaaagaaa cattttgagca gttttttgat gctacattta cctatttcac tcttaaatac    3600
tatttcctat gtaatatgta atttagaata tgttacctac tcaaatcaat taggtgacat    3660
gtataagctt tcataaatta tgctagaaat gcacttactt ttcaaagcat gctatgtcaa    3720
aagatttcat tcttcctctt ctaggttatt acgcaccacc caccacgtat ccctgaaaag    3780
agagaaaaac acactaagcc aaagccaaag cagcaagtta tttattggat tctagctact    3840
caaattactt tttttttaat gttacgtttt tggagttta acgttttctg aacaacttgc      3900
aaattacatg catagagaga caggaattca tagtgggcct caatggaata tttatttgaa     3960
attagtaagg tggtaactag tctagagagc tcaccggtgg tttaggaatt aaaggaacgg    4020
tgggctggta atgaacgcca ttgattcttc gaacgcatgc gctaatgtta gaaggcccgc    4080
tagtaggaac gcacttctcc cgggtgcggc cgcatttaaa tactagttac caccttacta    4140
atttcaaata aatattccat tgaggcccac tatgaattcc tgtctctcta tgcatgtaat    4200
ttgcaagttg ttcagaaaac gttaaaactc caaaaacgta acattaaaaa aaagtaatt    4260 tgagtagcta gaatccaata aataacttgc tgctttggct ttggcttagt gtgttttct    4320 ctcttttcag ggatacgtgg tgggtggtgc gtaataacct agaagaggaa gaatgaaatc    4380
ttttgacata gcatgctttg aaaagtaagt gcatttctag cataatttat gaaagcttat    4440
acatgtcacc taattgattt gagtaggtaa catattctaa attacatatt acataggaaa    4500
tagtatttaa gagtgaaata ggtaaatgta gcatcaaaaa cttgctcaaa tgtttctttc    4560
tctgttacaa actgacaatt caaaatttat tattactacc ttactaattt caaataaata    4620
ttccatgtct ctctatgcaa gtaatttgca agttgttcag aaaacgttaa actccaaaaa    4680
acataacatt aaaaaaaaag taattttgagt agctagaatc caataaataa taccccaaaa    4740
agtttgaaac tgctgctgct gctgcttttg ctttggctta gagagtgtgg ttcctctctt    4800
ttctcaggga tacgtggtgc gtaaaaacct agaataggaa gaaggaaatc gtgaaaaatc    4860
taaagataat gacaactaca aaatgaatgg agagattaga gagagtgaaa tcatgaccat    4920
aaaacaaaaa gtaaccagca cgaaatgttg tgatcgtcct ctactgcggc attacagcca    4980
attgtttatc aatagagaga agtgctgata ttgtagctac tagctaggtg cctacaccta    5040
agccttcagg aaatctagaa atgaaaaagg atatataaat gcataattca atttcgggag    5100
```

```
tttcttttcc tcaacaaata tgatgaaccc cacatgaaat atcccgaggt gcaggcacaa     5160
tttaatttac ctcgagccta ggcgtacagc ccggctccaa ggccgtgggg tacgaacaaa     5220
agagtgcctc acatttgatg caatagctct gtaatgtttc attcatttgc ttatttcggc     5280 cttgttttc tcgtattcta tgggctgatg tctcatatgg acttttcta ctagagagcc       5340 tacgttactt taccattata ttgtattctt tgagacatta ttattatttt tttaccttttt    5400 gaggacactc tttttttgta tttgaaggaa tttattgttt attttgtttg aatatgtttt     5460
ggttggattt attcgattca tatatattat ataaagtaa ttatgttatt aagaaacgta      5520
gtaagaactt acaaatataa ggatcgaatc ccgaacttca tgcaaatcaa tttacaaccc     5580
acacaagttt aacattaaat taacgtgatt ggttagtaaa ttcatgtttc tctgtttaat     5640
ttgttgaatt gggtcccata tatatatagc gatcgcatat atatataggc gcgccaaatc     5700
gtgaagtttc tcatctaagc ccccatttgg acgtgaatgt agacacgtcg aaataaagat     5760
ttccgaatta gaataatttg tttattgctt tcgcctataa atacgacgga tcgtaatttg     5820
tcgttttatc aaaatgtact ttcattttat aataacgctg cggacatcta catttttgaa     5880
ttgaaaaaaa attggtaatt actctttctt tttctccata ttgaccatca tactcattgc     5940
tgatccatgt agatttcccg gacatgaagc catttacaat tgaatatatc ctgccgccgc     6000
tgccgctttg cacccggtgg agcttgcatg ttggtttcta cgcagaactg agccggttag     6060
gcagataatt ccattgaga actgagccat gtgcaccttc cccccaacac ggtgagcgac      6120
ggggcaacgg agtgatccac atgggacttt t                                    6151

<210> SEQ ID NO 6
<211> LENGTH: 6689
<212> TYPE: DNA
<213> ORGANISM: Artificial
<220> FEATURE:
<223> OTHER INFORMATION: Cassette

<400> SEQUENCE: 6 aggattttc ggcgctgcgc tacgtccgcg accgcgttga gggatcaagc cacagcagcc        60
cactcgacct tctagccgac ccagacgagc caagggatcc ttttggaatg ctgctccgtc      120
gtcaggcttt ccgacgtttg ggtggttgaa cagaagtcat tatcgcacgg aatgccaagc     180
actcccgagg ggaaccctgt ggttggcatg cacatacaaa tggacgaacg gataaacctt     240 ttcacgcct tttaaatatc cgattattct aataaacgct cttttctctt aggtttaccc      300
gccaatatat cctgtcaaac actgatagtt taaactgaag gcgggaaacg acaatctgat     360
ccccatcaag ctagcttctg caggtcctgc tcgagcggcc gcctgataca cacttaagca     420
tcatgtggaa agccaaagac aattggagcg agactcaggg tcgtcataat accaatcaaa     480
gacgtaaaac cagacgcaac ctctttggtt gaatgtaatg aaagggatgt gtcttggtat     540
gtatgtacga ataacaaaag agaagatgga attagtagta gaaatatttg ggagcttttt    600
aagcccttca gtgtgctttt ttatcttatt gatatcatcc atttgcgttg tttaatgcgt    660
ctctagatat gttcctatat ctttctcagt gtctgataag tgaaatgtga gaaaaccata    720
ccaaaccaaa atattcaaat cttatttta ataatgttga atcactcgga gttgccacct     780
tctgtgccaa ttgtgctgaa tctatcacac tagaaaaaaa catttcttca aggtaatgac    840
ttgtggacta tgttctgaat tctcattaag ttttatttt ctgaagttta agttttacc     900 ttctgttttg aaatatatcg ttcataagat gtcacgccag gacatgagct acacatcgca    960
catagcatgc agatcaggac gatttgtcac tcacttcaaa cacctaagag cttctctctc   1020
```

```
acagcgcaca cacatatgca tgcaatattt acacgtgatc gccatgcaaa tctccattct   1080
cacctataaa ttagagcctc ggcttcactc tttactcaaa ccaaaactca tcactacaga   1140
acatacacaa gataattccc taggccaaga tgttgaagct ctcttcttcc cgaagcccat   1200
tggcccgcat tcccacccgg cccaggccca actccattcc tccccggata attgtggttt   1260
cctcctcatc cagcaaggtt aatccactca aaacagaggc ggtggtttct cggggctgg   1320 ctgaccggct ccggctgggc agcttgaccg aggacgggct ttcgtataag gagaagttca   1380
tagtgagatg ctatgaggtt gggattaaca agaccgctac tgttgagact attgccaacc   1440
tcttgcagga ggttggatgc aatcacgccc aaagcgttgg atattcgacg ggtgggtttt   1500
cgacaacccc taccatgaga aaattgcgtc tgatatgggt tactgctcgc atgcacatcg   1560
aaatctacaa atatccagct tggagtgatg tggtggaaat agagtcgtgg ggccagggtg   1620
aaggaaaaat cggaaccaga cgtgattgga ttctgagaga ctatgccact ggtcaagtta   1680
ttggccgagc tactagcaag tgggtaatga tgaaccaaga caccaggcga cttcaaaaag   1740
tcgatgttga tgttcgtgat gagtacttgg ttcactgtcc aagagaactc agattggcat   1800
ttccagagga aaataatagc agcttgaaga aaatttcaaa acttgaagat ccttctcaat   1860
attcgaagct ggggcttgtg cctagaagag cagatctgga catgaatcaa catgttaata   1920
atgtcaccta tattggatgg gtgttggaga gcatgcctca agaaatcatt gatacccatg   1980
aactgcaaac cataacatta gactacagac gggaatgcca acatgatgat gtggttgatt   2040
ccttgactag tccagagcct tctgaagatg ctgaagcagt tttcaaccat aatggaacaa   2100
atgggtctgc aaatgtgagc gccaacgacc atggatgccg caactttctg catctactaa   2160
gattgtcggg caatggactt gaaatcaacc gtggtcgtac tgagtggaga aagaaaccta   2220
caagatgact cgagagtgtg tataccacgg tgatatgagt gtggttgttg atgtatgtta   2280
acactacata gtcatggtgt gtgttccata aataatgtac taatgtaata agaactactc   2340
cgtagacggt aataaaagag aagtttttt ttttactctt gctactttcc tataaagtga   2400
tgattaacaa cagatacacc aaaaagaaaa caattaatct atattcacaa tgaagcagta   2460
ctagtctatt gaacatgtca gatttttctt ttctaaatgt ctaattaagc cttcaaggct   2520
agtgatgata aaagatcatc caatgggcgg ccgcgggtcc ggcggccgcg gtacggtcga   2580
ctctagagga tccccggcaa aaacatttaa tacgtattat ttaagaaaaa aatatgtaat   2640
aatatattta tattttaata tctattctta tgtattttt aaaaatctat tatatattga   2700
tcaactaaaa tattttata tctacactta ttttgcattt ttatcaattt tcttgcgttt   2760
tttggcatat ttaataatga ctattcttta ataatcaatc attattctta catggtacat   2820
attgttggaa ccatatgaag tgtccattgc atttgactat gtggatagtg ttttgatcca   2880
ggcctccatt tgccgcttat taattaattt ggtaacagtc cgtactaatc agttacttat   2940
ccttcctcca tcataattaa tcttggtagt ctcgaatgcc acaacactga ctagtctctt   3000
ggatcataag aaaaagccaa ggaacaaaag aagacaaaac acaatgagag tatcctttgc   3060
atagcaatgt ctaagttcat aaaattcaaa caaaaacgca atcacacaca gtggacatca   3120
cttatccact agctgatcag gatcgccgcg tcaagaaaaa aaaactggac cccaaaagcc   3180
atgcacaaca cacgtactc acaaggtgt caatcgagca gcccaaaaca ttcaccaact   3240
caacccatca tgagcccaca catttgttgt ttctaaccca acctcaaaact cgtattctct   3300 tccgccacct catttttgtt tatttcaaca cccgtcaaac tgcatgccac cccgtggcca   3360
```

```
aatgtccatg catgttaaca agacctatga ctataaatat ctgcaatctc ggcccaggtt    3420
ttcatcatca agaaccgggt accgagctcg agcgtacgcc taggctcgag gtaaattaaa    3480
ttgtgcctgc acctcgggat atttcatgtg gggttcatca tatttgttga ggaaaagaaa    3540
ctcccgaaat tgaattatgc atttatatat ccttttttcat ttctagattt cctgaaggct    3600
taggtgtagg cacctagcta gtagctacaa tatcagcact tctctctatt gataaacaat    3660
tggctgtaat gccgcagtag aggacgatca caacatttcg tgctggttac ttttttgtttt    3720 atggtcatga tttcactctc tctaatctct ccattcattt tgtagttgtc attatcttta    3780 gattttcac gatttccttc ttcctattct aggttttttac gcaccacgta tccctgagaa    3840
aagagaggaa ccacactctc taagccaaag caaaagcagc agcagcagca gtttcaaact    3900 tttgggtta ttatttattg gattctagct actcaaatta cttttttttt aatgttatgt    3960
tttttggagt ttaacgttttt ctgaacaact tgcaaattac ttgcatagag agacatggaa    4020
tatttatttg aaattagtaa ggtagtaata ataaattttg aattgtcagt ttgtaacaga    4080
gaaagaaaca tttgagcaag ttttttgatgc tacatttacc tatttcactc ttaaatacta    4140
tttcctatgt aatatgtaat ttagaatatg ttacctactc aaatcaatta ggtgacatgt    4200
ataagctttc ataaattatg ctagaaatgc acttactttt caaagcatgc tatgtcaaaa    4260
gatttcattc ttcctcttct aggttattac gcaccaccca ccacgtatcc ctgaaaagag    4320
agaaaaacac actaagccaa agccaaagca gcaagttatt tattggattc tagctactca    4380
aattactttt tttttaatgt tacgtttttg gagttttaac gttttctgaa caacttgcaa    4440
attacatgca tagagagaca ggaattcata gtgggcctca atggaatatt tatttgaaat    4500
tagtaaggtg gtaactagtc tagagagctc accggtggtt taggaattaa aggaacggtg    4560
ggctggtaat gaacgccatt gattcttcga acgcatgcgc taatgttaga aggcccgcta    4620
gtaggaacgc acttctcccg ggtgcggccg catttaaata ctagttacca ccttactaat    4680
ttcaaataaa tattccattg aggcccacta tgaattcctg tctctctatg catgtaatttt    4740 gcaagttgtt cagaaaacgt taaaactcca aaaacgtaac attaaaaaaa aagtaatttg    4800
agtagctaga atccaataaa taacttgctg cttttggcttt ggcttagtgt gttttttctct    4860 cttttcaggg atacgtggtg ggtggtgcgt aataacctag aagaggaaga atgaaatctt    4920
ttgacatagc atgctttgaa aagtaagtgc atttctagca taatttatga aagcttatac    4980
atgtcaccta attgatttga gtaggtaaca tattctaaat tacatattac ataggaaata    5040
gtatttaaga gtgaaatagg taaatgtagc atcaaaaact tgctcaaatg tttctttctc    5100
tgttacaaac tgacaattca aaatttatta ttactacctt actaatttca aataaatatt    5160
ccatgtctct ctatgcaagt aatttgcaag ttgttcagaa aacgttaaac tccaaaaaac    5220
ataacattaa aaaaaagta atttgagtag ctagaatcca ataaataata acccaaaaag    5280
tttgaaactg ctgctgctgc tgcttttgct ttggcttaga gagtgtggtt cctctctttt    5340
ctcagggata cgtggtgcgt aaaaacctag aataggaaga aggaaatcgt gaaaaatcta    5400
aagataatga caactacaaa atgaatggag agattagaga gagtgaaatc atgaccataa    5460
aacaaaaagt aaccagcacg aaatgttgtg atcgtcctct actgcggcat tacagccaat    5520
tgtttatcaa tagagagaag tgctgatatt gtagctacta gctaggtgcc tacacctaag    5580
ccttcaggaa atctagaaat gaaaaggat atataaatgc ataattcaat tcgggagtt    5640 tcttttcctc aacaaatatg atgaaccca catgaaatat cccgaggtgc aggcacaatt    5700
taatttacct cgagcctagg cgtacagccc ggctccaagg ccgtggggta cgaacaaaag    5760
```

-continued

```
agtgcctcac atttgatgca atagctctgt aatgtttcat tcatttgctt atttcggcct    5820
tgttttctc gtattctatg ggctgatgtc tcatatggga cttttctact agagagccta     5880
cgttacttta ccattatatt gtattctttg agacattatt attattttt tacctttttga    5940
ggacactctt tttttgtatt tgaaggaatt tattgtttat tttgtttgga atatgtttgg    6000
ttggatttat tcgattcata tatattatat aaaagtaatt atgttattaa gaaacgtagt    6060
aagaacttac aaatataagg atcgaatccc gaacttcatg caaatcaatt tacaacccac    6120
acaagtttaa cattaaatta acgtgattgg ttagtaaatt catgtttctc tgtttaattt    6180
gttgaattgg gtcccatata tatatagcga tcgcatatat ataggcgc gccaaatcgt      6240
gaagtttctc atctaagccc ccatttggac gtgaatgtag acacgtcgaa ataagattt     6300
ccgaattaga ataatttgtt tattgctttc gcctataaat acgacggatc gtaatttgtc    6360
gttttatcaa aatgtacttt cattttataa taacgctgcg gacatctaca ttttgaatt     6420
gaaaaaaat tggtaattac tctttctttt tctccatatt gaccatcata ctcattgctg     6480
atccatgtag atttcccgga catgaagcca tttacaattg aatatatcct gccgccgctg    6540
ccgctttgca cccggtggag cttgcatgtt ggtttctacg cagaactgag ccggttaggc    6600
agataatttc cattgagaac tgagccatgt gcaccttccc cccaacacgg tgagcgacgg    6660
ggcaacggag tgatccacat gggactttt                                      6689
```

<210> SEQ ID NO 7
<211> LENGTH: 6474
<212> TYPE: DNA
<213> ORGANISM: Artificial
<220> FEATURE:
<223> OTHER INFORMATION: Cassette

<400> SEQUENCE: 7

```
aggattttc ggcgctgcgc tacgtccgcg accgcgttga gggatcaagc cacagcagcc       60
cactcgacct tctagccgac ccagacgagc caagggatct ttttggaatg ctgctccgtc     120
gtcaggcttt ccgacgtttg ggtggttgaa cagaagtcat tatcgcacgg aatgccaagc     180
actcccgagg ggaaccctgt ggttggcatg cacatacaaa tggacgaacg gataaacctt     240
ttcacgccct tttaaatatc cgattattct aataaacgct cttttctctt aggtttaccc     300
gccaatatat cctgtcaaac actgatagtt taaactgaag gcgggaaacg acaatctgat     360
ccccatcaag ctagcttctg caggtcctgc tcgagcggcc gctctagaac tagtggatcc     420
aacgacgtcg ttttggtgtt attaacggcc ttaaaacgga ttaaatccat aatccgtcag     480
tcaactaggg ttacggatgg tcaacggcgt ttttgcataa cggaggcaca gttcaggctt     540
aacggagtgg accgaatggc ttttttaggaa gtttgtaacc gggatctctt gtttatgatg    600
tatttgtccc cgtcggctat tgtttaggcc gttttttccta tatattggaa ataactattg    660
tccagacgag ttacttctcc aacatatcaa gaaatgttac aaagaagtgt acaaaaatg     720
tgttactaag ccataaaact caaagcatat atcttagacc ctaagcctaa accctagaac    780
tttctaggac gttataacct tgtcctttct ttagtttcct ttaaaggcct tcgtatcata    840
agttttattt ttgcttaata ctaacactag aaataatcaa cataaactag gttaagtcgt   900
ggatctaatt ttattgtgaa aatgtaattg cttctcttaa gaaagattc atagcaaaat     960
attcgcatct ttcttgtgaa tcatcttttg ttttttgggc tattaaagaa aaattgaact   1020
catgaaatgg tgacaacttt attctagagg taacagaaca aaaatatagg aacaacacgt   1080
```

```
gttgttcata aactacacgt ataatactca agaagatgaa tctttataag aatttagttt    1140
tctcatgaaa acataaaaaa ttttgtcaat tgaaagtgac agttgaagca aaggaacaaa    1200
aggatggttg gtgatgatgc tgaaatgaaa atgtgtcatt catcaaatac taaatactac    1260
attacttgtc actgcctact ctcctatttt cctccgccac ccattttgga cccacgagcc    1320
ttccatttaa accctctctc gtgctattca ccagaagaga agccaagaga gagagagaga    1380
gattgtgctg aggatcattg tcttcttcat cgttattaac gtaagttttt tttgaccact    1440
catatctaaa atctagtaca tgcaatagat taatgactgt tccttctttt gatattttca    1500
gcttcttcct aggccaagat gttgaagctc tcttcttccc gaagcccatt ggcccgcatt    1560
cccacccggc ccaggcccaa ctccattcct ccccggataa ttgtggtttc ctcctcatcc    1620
agcaaggtta atccactcaa aacagaggcg gtggtttctt cggggctggc tgaccggctc    1680
cggctgggca gcttgaccga ggacgggctt tcgtataagg agaagttcat agtgagatgc    1740
tatgaggttg ggattaacaa gaccgctact gttgagacta ttgccaacct cttgcaggag    1800
gttggatgca atcacgccca aagcgttgga tattcgacgg gtgggttttc gacaacccct    1860
accatgagaa aattgcgtct gatatgggtt actgctcgca tgcacatcga aatctacaaa    1920
tatccagctt ggagtgatgt ggtggaaata gagtcgtggg gccagggtga aggaaaaatc    1980
ggaaccagac gtgattggat tctgagagac tatgccactg gtcaagttat tggccgagct    2040
actagcaagt gggtaatgat gaaccaagac accaggcgac ttcaaaaagt cgatgttgat    2100
gttcgtgatg agtacttggt tcactgtcca agagaactca gattggcatt tccagaggaa    2160
aataatagca gcttgaagaa aatttcaaaa cttgaagatc cttctcaata ttcgaagctg    2220
gggcttgtgc ctagaagagc agatctggac atgaatcaac atgttaataa tgtcacctat    2280
attggatggg tgttggagag catgcctcaa gaaatcattg atacccatga actgcaaacc    2340
ataacattag actacagacg ggaatgccaa catgatgatg tggttgattc cttgactagt    2400
ccagagcctt ctgaagatgc tgaagcagtt ttcaaccata atggaacaaa tgggtctgca    2460
aatgtgagcg ccaacgacca tggatgccgc aactttctgc atctactaag attgtcgggc    2520
aatggacttg aaatcaaccg tggtcgtact gagtggagaa agaaacctac aagatgactc    2580
gagagtgtgt ataccacggt gatatgagtg tggttgttga tgtatgttaa cactacatag    2640
tcatggtgtg tgttccataa ataatgtact aatgtaataa gaactactcc gtagacggta    2700
ataaaagaga agttttttttt tttactcttg ctactttcct ataaagtgat gattaacaac    2760
agatacacca aaaagaaaac aattaatcta tattcacaat gaagcagtac tagtctattg    2820
aacatgtcag attttctttt tctaaatgtc taattaagcc ttcaaggcta gtgatgataa    2880
aagatcatcc aatgggcggc cgcgggtccg gcggccgcgg tacggtcgac tctagaggat    2940
ccccggcaaa acatttaat acgtattatt taagaaaaaa atatgtaata atatatttat     3000
attttaatat ctattcttat gtattttta aaaatctatt atatattgat caactaaaat    3060
atttttatat ctacacttat tttgcatttt tatcaatttt cttgcgtttt ttggcatatt    3120
taataatgac tattctttaa taatcaatca ttattcttac atggtacata ttgttggaac    3180
catatgaagt gtccattgca tttgactatg tggatagtgt tttgatccag gcctccatt    3240 gccgcttatt aattaatttg gtaacagtcc gtactaatca gttacttatc cttcctccat    3300
cataattaat cttggtagtc tcgaatgcca caacactgac tagtctcttg gatcataaga    3360 aaagccaag gaacaaaga agacaaaaca caatgagagt atcctttgca tagcaatgtc    3420
taagttcata aaattcaaac aaaaacgcaa tcacacacag tggacatcac ttatccacta    3480
```

```
gctgatcagg atcgccgcgt caagaaaaaa aaactggacc ccaaaagcca tgcacaacaa    3540
cacgtactca caaggtgtc  aatcgagcag cccaaaacat tcaccaactc aacccatcat    3600
gagcccacac atttgttgtt tctaacccaa cctcaaactc gtattctctt ccgccacctc    3660 attttttgttt atttcaacac ccgtcaaact gcatgccacc ccgtggccaa atgtccatgc   3720
atgttaacaa gacctatgac tataaatatc tgcaatctcg cccaggtttt tcatcatcaa    3780
gaaccgggta ccgagctcga gcgtacgcct aggctcgagg taaattaaat tgtgcctgca    3840
cctcgggata tttcatgtgg ggttcatcat atttgttgag gaaaagaaac tcccgaaatt   3900
gaattatgca tttatatatc cttttttcatt tctagatttc ctgaaggctt aggtgtaggc   3960
acctagctag tagctacaat atcagcactt ctctctattg ataaacaatt ggctgtaatg    4020
ccgcagtaga ggacgatcac aacatttcgt gctggttact ttttgtttta tggtcatgat    4080
ttcactctct ctaatctctc cattcatttt gtagttgtca ttatctttag attttttcacg   4140 taacagagaa agaaacattt gagcaagttt ttgatgctac atttacctat ttcactctta    4200
aatactattt cctatgtaat atgtaattta gaatatgtta cctactcaaa tcaattaggt    4260
gacatgtata agctttcata aattatgcta gaaatgcact tacttttcaa agcatgctat    4320
gtcaaaagat ttcattcttc ctcttctagg ttattacgca ccacccacca cgtatccctg    4380
aaaagagaga aaaacacact aagccaaagc caaagcagca agttatttat tggattctag    4440
ctactcaaat tactttttttt ttaatgttac gttttttggag ttttaacgtt ttctgaacaa   4500
cttgcaaatt acatgcatag agagacagga attcatagtg ggcctcaatg gaatatttat    4560
ttgaaattag taaggtggta actagtctag agagctcacc ggtggtttag gaattaaagg    4620
aacggtgggc tggtaatgaa cgccattgat tcttcgaacg catgcgctaa tgttagaagg    4680
cccgctagta ggaacgcact tctcccgggt gcggccgcat ttaaatacta gttaccacct    4740 tactaattttc aaataaatat tccattgagg cccactatga attcctgtct ctctatgcat   4800
gtaatttgca agttgttcag aaaacgttaa aactccaaaa acgtaacatt aaaaaaaaag    4860
taatttgagt agctagaatc caataaataa cttgctgctt tggctttggc ttagtgtgtt    4920
tttctctctt ttcagggata cgtggtgggt ggtgcgtaat aacctagaag aggaagaatg    4980
aaatcttttg acatagcatg ctttgaaaag taagtgcatt tctagcataa tttatgaaag    5040
cttatacatg tcacctaatt gatttgagta ggtaacatat tctaaattac atattacata    5100
ggaaatagta tttaagagtg aaataggtaa atgtagcatc aaaaacttgc tcaaatgttt    5160 cttttctctgt tacgtgaaaa atctaaagat aatgacaact acaaaatgaa tggagagatt   5220
agagagagtg aaatcatgac cataaaacaa aaagtaacca gcacgaaatg ttgtgatcgt    5280
cctctactgc ggcattacag ccaattgttt atcaatagag agaagtgctg atattgtagc    5340
tactagctag gtgcctacac ctaagccttc aggaaatcta gaaatgaaaa aggatatata    5400
aatgcataat tcaatttcgg gagtttcttt tcctcaacaa atatgatgaa ccccacatga    5460
aatatcccga ggtgcaggca caatttaatt tacctcgagc ctaggcgtac agcccggctc    5520
caaggccgtg gggtacgaac aaaagagtgc ctcacatttg atgcaatagc tctgtaatgt    5580
ttcattcatt tgcttatttc ggccttgttt ttctcgtatt ctatgggctg atgtctcata    5640
tgggactttt ctactagaga gcctacgtta ctttaccatt atattgtatt ctttgagaca    5700
ttattattat ttttttacct tttgaggaca ctctttttttt gtatttgaag gaatttattg   5760
tttattttgt ttggaatatg tttggttgga tttattcgat tcatatatat tatataaaag    5820
```

```
taattatgtt attaagaaac gtagtaagaa cttacaaata taaggatcga atcccgaact    5880
tcatgcaaat caatttacaa cccacacaag tttaacatta aattaacgtg attggttagt    5940
aaattcatgt ttctctgttt aatttgttga attgggtccc atatatatat agcgatcgca    6000
tatatatata ggcgcgccaa atcgtgaagt ttctcatcta agcccccatt tggacgtgaa    6060
tgtagacacg tcgaaataaa gatttccgaa ttagaataat ttgtttattg ctttcgccta    6120
taaatacgac ggatcgtaat ttgtcgtttt atcaaaatgt actttcattt tataataacg    6180
ctgcggacat ctacattttt gaattgaaaa aaaattggta attactcttt cttttctcc    6240 atattgacca tcatactcat tgctgatcca tgtagatttc ccggacatga agccatttac    6300
aattgaatat atcctgccgc cgctgccgct ttgcacccgg tggagcttgc atgttggttt    6360
ctacgcagaa ctgagccggt taggcagata atttccattg agaactgagc catgtgcacc    6420
ttccccccaa cacggtgagc gacggggcaa cggagtgatc cacatgggac tttt          6474
```